US010563178B2

(12) United States Patent
He

(10) Patent No.: US 10,563,178 B2
(45) Date of Patent: Feb. 18, 2020

(54) PIV5-BASED AMPLIFYING VIRUS-LIKE PARTICLES

(71) Applicant: University of Georgia Research Foundation, Inc., Athens, GA (US)

(72) Inventor: Biao He, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 115 days.

(21) Appl. No.: 15/556,158

(22) PCT Filed: Apr. 28, 2016

(86) PCT No.: PCT/US2016/029884
§ 371 (c)(1),
(2) Date: Sep. 6, 2017

(87) PCT Pub. No.: WO2016/176510
PCT Pub. Date: Nov. 3, 2016

(65) Prior Publication Data
US 2018/0044644 A1    Feb. 15, 2018

Related U.S. Application Data

(60) Provisional application No. 62/153,598, filed on Apr. 28, 2015.

(51) Int. Cl.
| | |
|---|---|
| *C12N 7/00* | (2006.01) |
| *A61K 48/00* | (2006.01) |
| *C07K 14/005* | (2006.01) |
| *C12N 9/22* | (2006.01) |
| *C12N 15/11* | (2006.01) |

(52) U.S. Cl.
CPC ............ *C12N 7/00* (2013.01); *A61K 48/0008* (2013.01); *C07K 14/005* (2013.01); *C12N 9/22* (2013.01); *C12N 15/11* (2013.01); *C12N 2310/20* (2017.05); *C12N 2760/16122* (2013.01); *C12N 2760/18723* (2013.01); *C12N 2760/18743* (2013.01)

(58) Field of Classification Search
CPC ..................................................... C12N 7/00
See application file for complete search history.

(56) References Cited

U.S. PATENT DOCUMENTS

| | | |
|---|---|---|
| 2003/0170266 A1 | 9/2003 | Kitazato et al. |
| 2005/0048030 A1* | 3/2005 | Pickles .............. C07K 14/4712 424/93.2 |
| 2015/0086588 A1 | 3/2015 | He |

FOREIGN PATENT DOCUMENTS

| | | | |
|---|---|---|---|
| WO | 9946278 | 9/1999 | |
| WO | WO2013/112720 | * 8/2013 | ........... A61K 39/155 |

OTHER PUBLICATIONS

Precious et al. (Journal of Virology, Dec. 1995; 69(2): 8001-8010). (Year: 1995).*
Griesenbach et al. (Human Gene Therapy 26:266-275 (May 2015) [published online Apr. 1, 2015]). (Year: 2015).*
Baumgartner et al., "Persistent infection of Vero cells by paramyxoviruses. A morphological and immunoelectron microscopic investigation," Intervirology, 27(4): 218-223, 1987.
Binn et al., "Viruses Recovered from Laboratory Dogs with Respiratory Disease," Exp Biol Med, 126(1):140-145, 1967.
Chantziandreou et al., "Relationships and host range of human, canine, simian and porcine isolates of simian virus 5 (parainfulenza virus 5)," J Gen Virol, 85:3007-3016, 2004.
Cohn et al., "T cell responses to the paramyxovirus simian virus 5: studies in multiple sclerosis and normal populations," Pathobiology, 64(3): 131-135, 1996.
Donnely et al., "Analysis of the aphthovirus 2A/2B polyprotein 'cleavage' mechanism indicates not a proteolytic reaction, but a novel translational effect: a putative ribosomal 'skip'," J Gen Virol, 82(Pt 5): 1013-25, 2001.
Evermann et al., "Isolation of a paramyxovirus from the cerebrospinal fluid of a dog with posterior paresis," J Am Vet Med Assoc, 177(11): 1132-1134, 1980.
Evermann et al., "Properties of an encephalitogenic canine parainfluenza virus," Arch Virol, 68(3-4):165-172, 1981.
Guan et al., "H5N1 influenza: A protean pandemic threat," Proc Natl Acad Sci, 101(21): 8156-8161, 2004.
He et al., "Recovery of Infectious SV5 from Cloned DNA and Expression of a Foreign Gene," Virology, 237(2): 249-260, 1997.
He et al., "The paramyxovirus SV5 small hydrophobic (SH) protein is not essential for virus growth in tissue culture cells," Virology, 250(1): 30-40, 1998.
He et al., "The SH Integral Membrane Protein of the Paramyxovirus Simian Virus 5 Is Required to Block Apoptosis in MDBK Cells," J Virol, 75(9): 4068-4079, 2001.
Hsiung et al. "Studies of Paraninfluenza viruses: III. Antibody responses of different animal species after immunization," J Immunol, 94(1): 67-73, 1965.

(Continued)

*Primary Examiner* — Scott Long
(74) *Attorney, Agent, or Firm* — Smith Gambrell & Russell LLP

(57) ABSTRACT

Compositions, methods of use and methods of manufacture are provided for PIV5-based amplifying VLP (AVLP) that can deliver an expressible heterologous nucleotide sequence in target cells without producing progeny, and which demonstrate useful safety and therapeutic efficacy in multiple animal and human health applications, such as vaccination, gene therapy and cancer therapy.

15 Claims, 28 Drawing Sheets

(56) References Cited

OTHER PUBLICATIONS

Li et al., "Recombinant Parainfluenza Virus 5 Expressing Hemagglutinin of Influenza A Virus H5N1 Protected Mice against Lethal Highly Pathogenic Avian Influenza Virus H5N1 Challenge," J Virol, 87(1): 354-362, 2013.

Lin et al., "Induction of Apoptosis by Paramyxovirus Simian Virus 5 Lacking a Small Hydrophobic Gene," J Virol, 77(6): 3371-3383, 2003.

Lin et al., "The role of simian virus 5 V protein on viral RNA synthesis," Virology, 338: 270-280, 2005.

Lippincott, Williams, and Wilkins., Lamb et al., "Paramyxoviridae: the viruses and their replication," Mol Biosci, 5th Ed, 1449-1496, 2007.

McCandlish et al., "A study of dogs with kennel cough," Vet Rec, 102:293-301, 1978.

Paterson et al., "Fusion Protein of the Paramyxovirus SV5: Destabilizing and Stabilizing Mutants of Fusion Activation," Virology, 270(1): 17-30, 2000.

Sturm-Ramirez et al., "Reemerging H5N1 Influenza Viruses in Hong Kong in 2002 Are Highly Pathogenic to Ducks," J Virol, 78(9), 4892-4901, 2004.

Sun et al., "Conserved Cysteine-Rich Domain of Paramyxovirus Simian Virus 5 V Protein Plays an Important Role in Blocking Apoptosis," J Virol, 78(10): 5068-5078, 2004.

Szymczak et al., "Correction of multi-gene deficiency in vivo using a single 'self-cleaving' 2A peptide-based retroviral vector," Nat Biotech, 22(5): 589-594, 2004.

Wansley et al., "Naturally occurring substitutions in the P/V gene convert the noncytopathic paramyxovirus simian virus 5 into a virus that induces alpha/beta interferon synthesis and cell death," J Virol, 76(20): 10109-10121, 2002.

Whelan et al., "Transcription and replication of nonsegmented negative-strand RNA viruses," Curr Top Microbiol Immunol, 283: 61-119, 2004.

Widjaja et al., "Matrix Gene of Influenza A Viruses Isolated from Wild Aquatic Birds: Ecology and Emergence of Influenza A Viruses," J Virol, 78(16): 8771-8779, 2004.

Pentecost et al., "Evidence for Ubiquitin-Regulated Nuclear and Subnuclear Trafficking . . . " Plos Pathogens, Mar. 17, 2015, vol. 11(3), p. 1-33.

Li et al., "Single-Dose Vaccination of a Recombinant Parainflueenza Virus 5 Expressing NP from H5N1 Virus . . . " Journal of Virology, 2013, vol. 87, p. 5985-03.

PCT Written Opinion of the International Searching Authority released by the U.S. Patent & Trademark Office as Int'l. Search Authority on Jul. 29, 2016; 6 pages.

Extended European Search Report issued by the European Patent Office for corresponding European application No. 16787193.8 dated Aug. 16, 2018; 8 pages.

Yoshizaki, M., et al., "Naked Sendai Virus Lacking all the Envelope-Related Genes: Reduced Cytopathogenicity and Immunogenicity" J of Gene Medicine, 1151-1159 (2006).

Wei, H., et al., "Developing a Platform System for Gene Delivery: Amplifying Virus-Like Particles (AVLP) as an Influenza Vaccine" Nature Partner Journals Vaccines (2017), 10 pages.

* cited by examiner

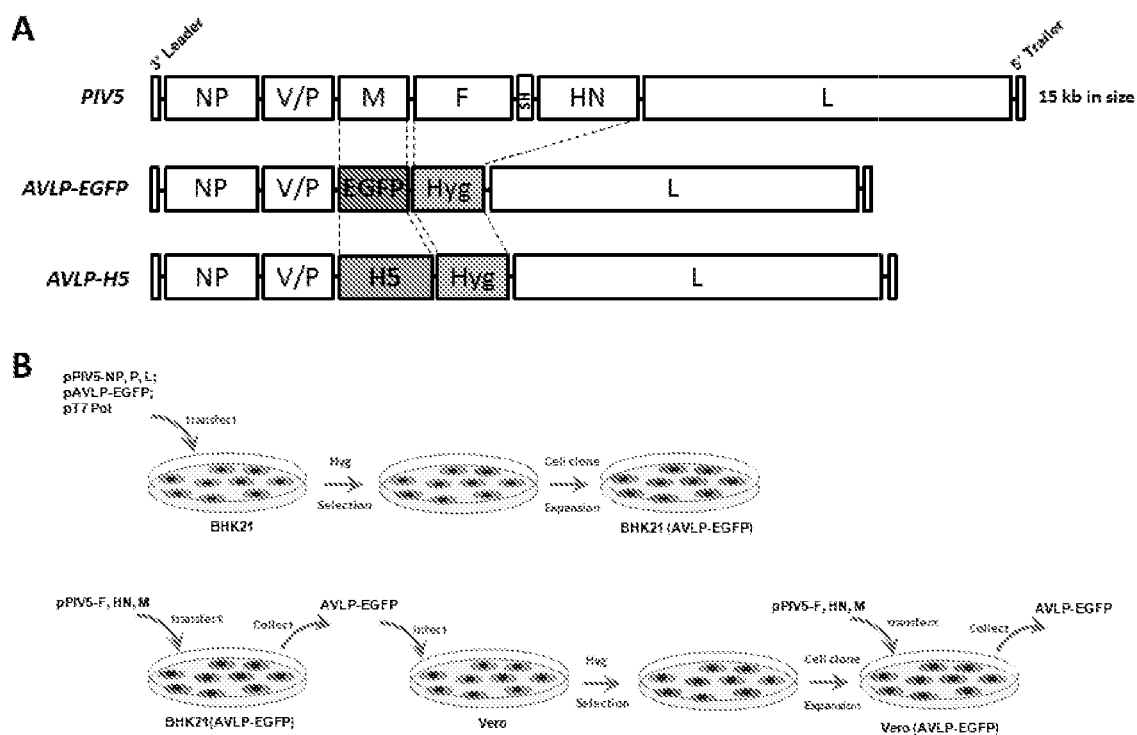
FIG. 1 (A & B)

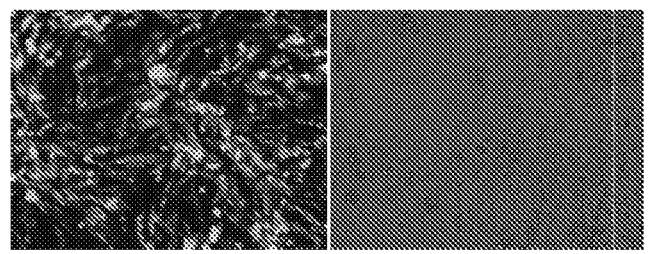
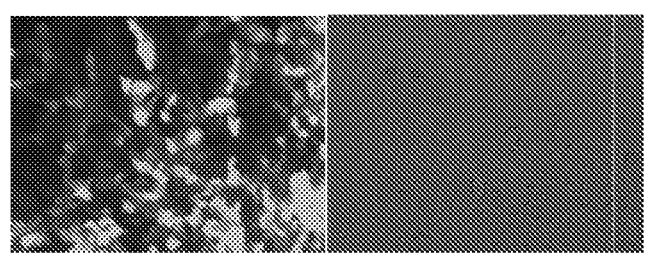
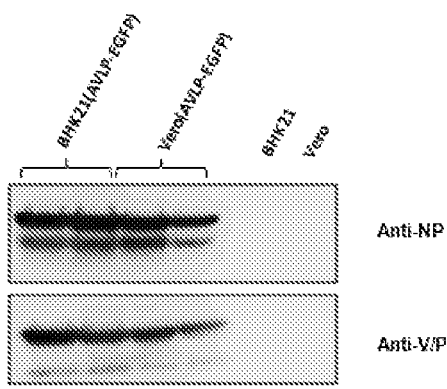
FIG. 1 (C & D)

A  Infection of Hela cells by F-M-HN packaged particles of AVLP-EGFP
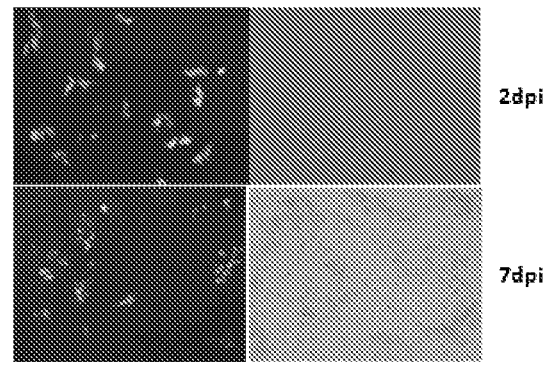
B  Infection of Vero cells by F-M-HN packaged particles of AVLP-EGFP
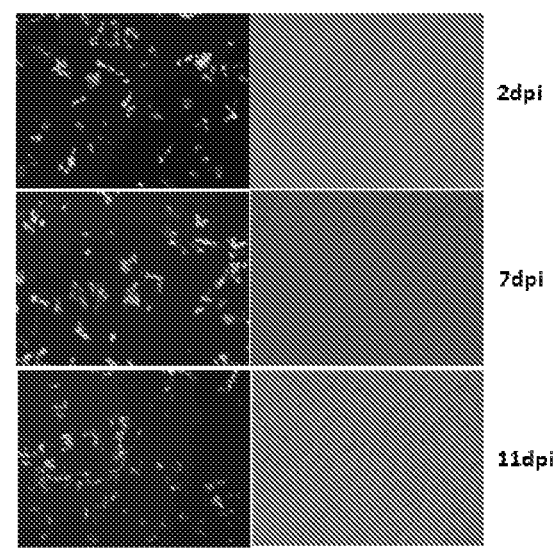
FIG. 2

Characterization of stable BHK21 cells carrying AVLP-BMP2

AVLP(HTL)-EGFP

AVLP(HT)-CART  | NP | V/P | CART | HygB-TK | L |

FIG. 22

PIV5-BASED AMPLIFYING VIRUS-LIKE PARTICLES

CROSS-REFERENCE TO RELATED APPLICATIONS

This application claims priority to and benefit of U.S. Provisional Patent Application No. 62/153,598, filed Apr. 28, 2015, which is hereby incorporated by reference herein in its entirety.

BACKGROUND

Several types of viruses, including retrovirus, adenovirus, adeno-associated virus (AAV), and herpes simplex virus, have been modified in the laboratory for therapeutic applications. However, each has limited applications for which it is best suited. For example, Retroviral vectors permanently integrate into the genome of the infected cell causing safety issues, and require mitotic cell division for transduction. Adenoviral vectors can deliver genes to a wide variety of dividing and nondividing cell types, but immune elimination of infected cells often limits gene expression in vivo. Herpes simplex virus can deliver large amounts of exogenous DNA; however, cytotoxicity and maintenance of transgene expression remain an obstacle. AAV infects many nondividing and dividing cell types, but has a limited DNA capacity. There plainly exists the need for a more flexible and versatile approach.

BRIEF SUMMARY OF THE INVENTION

The present disclosure relates to compositions, methods of use and methods of manufacture of, or for, Parainfluenza 5 (PIV5) virus-like particles (VLPs) which safely and effectively deliver expressible heterologous nucleotides of interest to a target cell without producing viral progeny (herein referred to as "Amplifying Virus-Like Particles" or "AVLPs").

In one embodiment, the disclosure comprises a isolated polynucleotide which comprises (i) at least a portion of each of PIV5 NP, V/P and L genes, and (ii) a heterologous non-PIV5 nucleotide sequence, wherein said polynucleotide lacks one or more of the PIV5 genes selected from the group consisting of M, F, SH and HN, or is incapable of expressing one or more of the PIV5 proteins selected from the group consisting of M, F, SH and HN.

In an aspect of this embodiment, the isolated polynucleotide can comprise PIV5 NP, V/P and L genes.

In yet another aspect of this embodiment, the isolated polynucleotide can lack PIV5 M gene or be incapable of expressing PIV5 M protein.

In another aspect of this embodiment, the heterologous non-PIV5 nucleotide sequence can be inserted between the V/P and L genes.

In yet another aspect of this embodiment, one or all of the M, F, SH and HN PIV5 genes are replaced with the heterologous nucleotide sequence.

In a further aspect of any of the above embodiments, the heterologous nucleotide sequence comprises a selection marker. In some embodiments, the selection marker can be Hyg or Hyg-TK.

In a further aspect of any of the above embodiments, the heterologous nucleotide sequence encodes a molecule selected from the group consisting of RNAi, shRNA, siRNA, antisense oligonucleotide, and ribozyme.

In a further aspect of any of the above embodiments, the heterologous nucleotide sequence is derived from a virus other than PIV5. In some embodiments, the heterologous nucleotide sequence is derived from a virus selected from the group consisting of influenza virus, RSV, and HIV. In one embodiment, the heterologous nucleotide sequence encodes influenza HA. In another embodiment, the heterologous nucleotide sequence encodes RSV F. In yet another embodiment, the heterologous nucleotide sequence encodes HIV Gag, Env or both.

In a further aspect of any of the above embodiments, the heterologous nucleotide sequence is a mammalian sequence. In one embodiment, the heterologous nucleotide sequence is a human sequence.

In a further aspect of any of the above embodiments, the heterologous nucleotide sequence encodes CFTR or NeuroD1 or BMP-2 protein.

In a further aspect of any of the above embodiments, the heterologous nucleotide sequence encodes Cas9 and Guide RNAs.

In a further aspect of any of the above embodiments, the heterologous nucleotide sequence encodes a secreted protein.

In a further aspect of any of the above embodiments, the heterologous polynucleotide further comprises a reporter gene. In some embodiments, the reporter gene encodes a luciferase or green fluorescent protein.

In another embodiment of the disclosure, the disclosure provides a vector comprising the polynucleotide as described in any of the above embodiments.

In yet another embodiment of the disclosure, the disclosure provides a host cell comprising the polynucleotide of any one of the above embodiments or said vector.

In still another embodiment of the disclosure, the disclosure provides an Amplifying Virus-Like Particle (AVLP) produced by said host cell.

In another embodiment of the disclosure, the disclosure provides an Amplifying Virus-Like Particle (AVLP) comprising the polynucleotide of any one of the above embodiments.

In still another embodiment of the disclosure, the disclosure provides a cell infected with said AVLP.

In another embodiment of the disclosure, the disclosure provides a method of treating a disease in a subject in need thereof comprising administering to said subject said AVLP. In a further aspect of this embodiment, the subject is human.

BRIEF DESCRIPTION OF FIGURES

Various features and advantages of the disclosure may be more readily understood with reference to the following description taken in conjunction with the accompanying figures. The figures listed below are not necessarily drawn to scale:

FIG. 1 shows AVLP expressing EGFP and H5 proteins (AVLP-EGFP, AVLP-H5) and development of stable cell lines, in accordance with an exemplary embodiment of the disclosure.

FIG. 2 shows infection of HeLa and Vero cells with AVLP-EGFP, in accordance with an exemplary embodiment of the disclosure.

Figure 3:
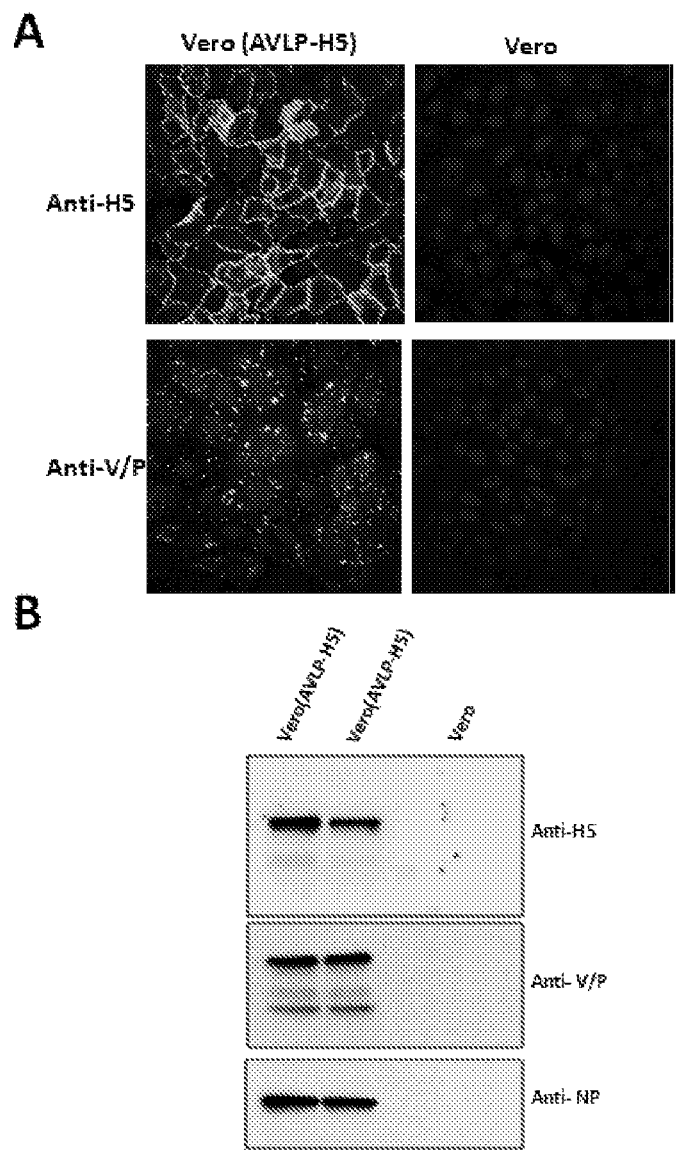
FIG. 3 shows the characterization of Vero (AVLP-H5) cell line, in accordance with an exemplary embodiment of the disclosure.

The phrase "pharmaceutically acceptable", as used in connection with compositions of the disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

The terms "treat" or "treatment" of a state, disorder or condition include:

(1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

As used herein, the term "parainfluenza virus 5" (PIV5) includes, for example and not limitation, strains KNU-11, CC-14, D277, 1168-1, and 08-1990. Non-limiting examples of PIV5 genomes are listed in GenBank Accession Nos. NC_006430.1, AF052755.1, KC852177.1, KP893891.1, KC237065.1, KC237064.1 and KC237063.1.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

The mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the disclosure are intended to be illustrative and not restrictive. Many suitable materials that would perform the same or a similar function as the materials described herein are intended to be embraced within the scope of the disclosure. Such other materials not described herein can include, but are not limited to, for example, materials that are developed after the time of the development of the disclosure.

Parainfluenza virus 5 (PIV5), a negative-stranded RNA virus, is a member of the Rubulavirus genus of the family Paramyxoviridae which includes many important human and animal pathogens such as mumps virus, human parainfluenza virus type 2 and type 4, Newcastle disease virus, Sendai virus, HPIV3, measles virus, canine distemper virus, rinderpest virus and respiratory syncytial virus. PIV5 was previously known as simian virus-5 (SV5) (Chatziandreou et al, 2004, J Gen Virol; 85:3007-3016). Although PIV5 was originally isolated from cultured primary monkey cells its natural host is the dog in which it causes kennel cough (McCandlish et al, 1978, Vet Rec; 102:293-301). Although PIV5 can infect humans (Cohn et al, 1996, Pathobiology; 64: 131-135), no known symptoms or diseases in humans have been associated with PIV5. Unlike most paramyxoviruses, PIV5 can infect normal cells with little cytopathic effect.

PIV5 in the present disclosure includes any of a variety of wild type PIV5 strains, mutant PIV5, or recombinant PIV5 (rPIV5). Wild type strains include, but are not limited to, the PIV5 strains W3A, WR (ATCC® Number VR-288™), canine parainfluenza virus strain 78-238 (ATCC number VR-1573) (Evermann et al, 1980, J Am Vet Med Assoc; 177: 1132-1134; and Evermann et al., 1981, Arch Virol; 68: 165-172), canine parainfluenza virus strain D008 (ATCC number VR-399) (Binn et al, 1967, Proc Soc Exp Biol Med; 126: 140-145), MIL, DEN, LN, MEL, cryptovirus, CPI+, CPI−, H221, 78524, Tl and SER. See, for example, Chatziandreou et al, 2004, J Gen Virol; 85 (Pt 10):3007-16; Choppin, 1964, Virology: 23:224-233; and Baumgartner et al, 1987, Intervirology; 27:218-223. Additionally, PIV5 strains used in commercial kennel cough vaccines, such as, for example, BI, FD, Merck, and Merial vaccines, may be used.

PIV5 genetic material may be constructed using any of a variety of methods, including, but not limited to, the reverse genetics system described in more detail in He et al. (Virology; 237(2):249-60, 1997).

PIV5 encodes eight viral proteins. Nucleocapsid protein (NP), phosphoprotein (P) and large RNA polymerase (L) protein are important for transcription and replication of the viral RNA genome. The V protein plays important roles in viral pathogenesis as well as viral RNA synthesis. The fusion (F) protein, a glycoprotein, mediates both cell-to-cell and virus-to-cell fusion in a pH-independent manner that is essential for virus entry into cells. The structures of the F protein have been determined and critical amino acid residues for efficient fusion have been identified. The hemagglutinin-neuraminidase (HN), another viral glycoprotein, is also involved in virus entry and release from the host cells. The matrix (M) protein plays an important role in virus assembly and budding. The hydrophobic (SH) protein is a 44-residue hydrophobic integral membrane protein and is oriented in membranes with its N terminus in the cytoplasm. For reviews of the molecular biology of paramyxoviruses see, for example, Whelan et al, 2004, Curr Top Microbiol Immunol; 283:61-119; and Lamb & Parks, (2006). Paramyxoviridae: the viruses and their replication. In Fields Virology, 5th edn, pp. 1449-1496. Edited by D. M. Knipe & P. M. Howley. Philadelphia, Pa.: Lippincott Williams & Wilkins. An oncolytic agent may have a mutation in one or more of these eight proteins.

PIV5 can infect human (Hsiung et al, 1965, J Immunol; 94:67-73), but it has not been associated with any known illness. PIV5 infects mice and hamsters but does not cause any symptoms in the animals. PIV5 can be grown in cells and released to media at a titer up to $8 \times 10^8$ pfu/ml, indicating its potential as a safe gene delivery vector and a possible cost effective way for mass production of the virus.

PIV5 can infect cells productively with little cytopathic effect (CPE) in many cell types. In some cell types, PIV5 infection causes formation of syncytia, i.e., fusion of many cells together, leading to cell death. A mutation may include one or more mutations that promote syncytia formation (see, for example Paterson et al, 2000, Virology; 270: 17-30).

PIV5 infection does not induce apoptosis (He et al, 2001, J Virol; 75:4068-4079. However, recombinant PIV5 lacking SH (rPIV5ASH) induces apoptosis in L929 cells through a tumor necrosis factor (TNF)-a mediated extrinsic apoptotic pathway (He et al, 2001, J Virol; 75:4068-4079; He et al, 1998, Virology; 250:30-40; and Lin et al, 2003, J Virol; 77:3371-3383).

The V protein of PIV5 plays a critical role in blocking apoptosis induced by virus. Recombinant PIV5 lacking the conserved cysteine-rich C-terminus (rPIV5VAC) of the V protein induces apoptosis in a variety of cells through an intrinsic apoptotic pathway, likely initiated through endoplasmic reticulum (ER)-stress (Sun et al, 2004, J Virol; 78: 5068-5078). Mutant recombinant PIV5 with mutations in the N-terminus of the V/P gene products, such as rPIV5-CPI-, also induce apoptosis (Wansley and Parks, 2002, J Virol; 76: 10109-10121).

The disclosure provides PIV5-based AVLP compositions, systems and methods for their use in multiple applications including functional genomics, drug discovery, target validation, protein production (e.g., therapeutic proteins, vaccines, monoclonal antibodies), gene therapy, and therapeutic treatments such as cancer therapy.

The disclosure relates to PIV5-based AVLP compositions, and constructs for their manufacture, which can be utilized to introduce expressible polynucleotide sequences of interest into host cells. In some embodiments, the PIV5-based AVLP composition is an isolated polynucleotide sequence that transcribes a single stranded RNA encoding a portion of a negative stranded PIV5 genome, wherein said polynucleotide sequence transcribes a single stranded RNA encoding at least a portion of the negative stranded NP, V/P and L genes, and wherein said polynucleotide sequence lacks, or is otherwise incapable of transcribing, one or more of the M, F, SH and HN genes, and wherein said polynucleotide sequence contains an heterologous non-PIV5 nucleotide sequence inserted between the V/P and L genes (e.g., FIG. 1A). In some embodiments, one or all of the M, F, SH and HN genes are completely removed and replaced with the expressible heterologous nucleotide sequence of interest. In some embodiments, the isolated polynucleotide comprises all of each of the NP, V/P and L genes. In some embodiments, the isolated polynucleotide comprises all of at least one of the NP, V/P and L genes.

In some embodiments, the PIV5-based AVLP compositions comprise at least one AVLP particle comprising an isolated polynucleotide as described herein. In other embodiments, the PIV5-based AVLP compositions comprise a plurality of AVLP particles comprising an isolated polynucleotide as described herein.

In some embodiments, the disclosure provides pharmaceutical compositions comprising PIV5-based AVLP compositions as described herein. Such pharmaceutical compositions may include pharmaceutically acceptable carriers and/or additional therapeutic agents as discussed herein. In some embodiments, the pharmaceutical composition comprises a therapeutically effective amount of the PIV5-based AVLP composition and/or additional therapeutic agents as described herein.

In further embodiments, additional regulatory sequences are placed upstream, downstream or within of the 3' leader and 5' trailer sequences in order to increase, improve, enhance, etc., replication, transcription and/or expression. In other embodiments, the AVLP composition further comprise transcription termination signals, such as a polyA signal that is effective to terminate transcription. In some embodiments, AVLP compositions further comprise other additional elements: 5' LTR, PBS, packaging sequence, splice donor (SD), origin of replication, optionally a central polypurine tract (PPT), RRE, MCS, splice acceptor (SA), and a modified minimally functional 3' LTR. Other elements which can be provided in the AVLP system include, e.g., a synthetic intron or other sequences utilized to stabilize mRNA, internal ribosome entry sites (IRES) to facilitate translation of two open reading frames from a single mRNA, selectable markers, and transcription termination signals (e.g., polyadenylation site). Other elements can be used to facilitate the expression of two open reading frames. One example is the 2A/2B peptide sequence which facilitates cleavage of a polypeptide at a predetermined site (Szymczak et al Nature Biotechnology 22: 589594, 2004). In this way, two polypeptide sequences that are separated by the self-cleaving 2A sequence can be produced from an AVLP system from a single open reading frame. Another example is to use Internal Ribosome Initiation Sequences or IRES elements such as those from Picornavirus or Foot and Mouth Disease virus are two non-limiting examples (Donnelly et al., J. Gen. Virol., 82:1013-1025, 2001).

The expressible heterologous nucleotide sequence of interest is essentially the AVLP payload. Here, the term "heterologous" means that the sequence is not derived from PIV5. The term "expressible" indicates that the polynucleotide sequence is capable of being transcribed in a cell, however it does not require—nor does it preclude—that the polynucleotide sequence be thereafter translated. The expressible heterologous nucleotide may encode one or more products, which may have the same or different mechanics of expression, and which may have the same or different intended functions when expressed in a cell.

Any expressible heterologous nucleotide sequence of interest can be inserted into the transfer vector without limitation, including, sequences coding for therapeutic proteins, enzymes, and antibodies, etc.; siRNA; anti-sense; microRNAs, aptamers; ribozymes, any gene inhibitory or silencing sequence; and any sequence which is to be delivered to a host cell via an AVLP system.

Sequences for expressible heterologous nucleotide of interest are known in the art, can be identified in GenBank and/or can otherwise be ascertained by well-known methods in the art including directly sequencing from a biological sample of interest.

The disclosure can be used in gene therapy and/or therapeutic approaches for the treatment of disease which involve the increase or decrease of a nucleotide sequence of interest in a host-cell. In these embodiments, the expressible heterologous nucleotide sequence may be derived from a mammalian genome. It may be particularly useful in some embodiments to have the expressible heterologous nucleotide sequence derived from a human genome, wherein expression of the wild-type RNA and/or protein can produce therapeutic effects in a patient. For example, the expressible heterologous nucleotide sequence can encode CFTR, NeuroD1, Cas9 and Guide RNAs, or any other such sequence. In other embodiments, the heterologous nucleotide sequence encodes a secreted protein. For example, the heterologous nucleotide sequence can encode BMP-2, or any other such sequence.

In other embodiments, the expressible heterologous nucleotide sequence responds to positive selection stimuli. For example, the heterologous nucleotide sequence may comprise Hyg and the positive selection stimuli is Hygromycin B. In other embodiments, the expressible heterologous nucleotide sequence also responds to negative selection stimuli. For example, the heterologous nucleotide sequence may comprise Hyg-TK and the negative selection stimuli may be Acyclovir or Ganciclovir. In further embodiments, it may be useful for the polynucleotide sequences to further comprise a reporter gene. For example, the report gene can be a luciferase or green fluorescent protein.

In some embodiments, AVLP expresses one or more nucleotide sequences (e.g., siRNAs) that modify the translation and/or transcription of a host-cell nucleotide sequence of interest within a host cell. In some embodiments, transcription and/or translation of the expressible heterologous nucleotide sequence is modified so that its nucleotide sequence is codon degenerated with respect to the endogenous gene in a cell. Additionally, the expressible heterologous nucleotide sequence can be modified so that it co-expresses inhibitory or silencing sequences capable of inhibiting or silencing a host-cell nucleotide sequence of interest within a host cell.

For example, AVLP can express siRNA targeted to beta-hemoglobin that can repress or silence sickle-hemoglobin in patients with sickle cell anemia. The same AVLP could also express a normal hemoglobin molecule that has been codon-degenerated at the site targeted by the siRNA. In this way erythroid cells expressing sickle globin can represses sickle globin expression, while expressing native hemoglobin and correct the genetic abnormality. The AVLP system would be delivered into a stem cell population that would give rise to erythroid cells expressing hemoglobin that would eventually become red cells. This approach can be tailored to treat a wide variety of diseases with AVLP compositions, including cancer, genetic disease and infectious diseases.

In other embodiments, the expressible heterologous nucleotide of interest generates a product that stabilizes host-cell RNA nucleotide sequences. Such a product can be inducible or continually expressed. For example, the 3' RhoB untranslated region (UTR) can stabilize target RNAs that express either toxic proteins or other proteins of interest in response to serum. Another example is linking the eotaxin 3' untranslated region to the target gene of interest, which normally has a low half-life, but is stabilized with the addition of TNF-alpha and IL-4 to the cells. Alternatively, sequences contained in 16 mer sequence in the 5' coding region of CYP2E 1 and CYP2B 1 mRNA destabilizes target RNAs in the presence of insulin. Upon the removal of insulin the target RNAs are stabilized and the proteins can be expressed (Trong et al., Biochem J., Dec. 23, 2004).

Further non-limiting examples of expressible heterologous sequences that can be used in the invented compositions and methods include sequences can produce proteins, including, for example, e.g., interferons (alpha, beta, gamma, epsilon), erythropoietin, Factor VIII, clotting factors, antibodies and fragments thereof (e.g., including single chain, Fab, and humanized), insulin, chemokines, cytokines, growth factors, angiogenesis modulatory factors, apoptosis modulatory factors, e.g., Growth Factors, including, e.g., Amphiregulin, B-lymphocyte stimulator, Interleukin 16 (IL16), Thymopoietin, TRAIL, Apo-2, Pre B cell colony enhancing factor, Endothelial differentiation-related factor 1 (EDF1), Endothelial monocyte activating polypeptide II, Macrophage migration inhibitory factor MIF, Natural killer cell enhancing factor (NKEFA), Bone morphogenetic protein 8 (osteogenic protein 2), Bone morphogenic protein 6, Connective tissue growth factor (CTGF), CGI-149 protein (neuroendocrine differentiation factor), Cytokine A3 (macrophage inflammatory protein 1-alpha), Glialblastoma cell differentiation-related protein (GBDR1), Hepatoma-derived growth factor, Neuromedin U-25 precursor, any tumor gene, oncogene, proto-oncogene or cell modulating gene (which can be found at condor.bcm.tmc.edu/oncogene), Vascular endothelial growth factor (VEGF), Vascular endothelial growth factor B (VEGF-B), T-cell specific RANTES precursor, Thymic dendritic cell-derived factor 1; Receptors, such as Activin A receptor, type II (ACVR2), β-signal sequence receptor (SSR2), CD14 monocyte LPS receptor, CD36 (collagen type 1/thrombospondin receptor)-like 2, CD44R (Hermes antigen gp90 homing receptor), G protein coupled receptor 9, Chemokine C×C receptor 4, Colony stimulating factor 2 receptor β(CSF2RB), FLT-3 receptor tyrosine kinase, Similar to transient receptor potential C precursor, Killer cell lectin-like receptor subfamily B, Low density lipoprotein receptor gene, low-affinity Fc-gamma receptor IIC, MCP-1 receptor, Monocyte chemoattractant protein 1 receptor (CCR2), Nuclear receptor subfamily 4, group A, member 1, Orphan G protein-coupled receptor GPRC5D, Peroxisome proliferative activated receptor gamma, Pheromore related-receptor (rat), Vasopressin-activated calcium mobilizing putative receptor, Retinoicxreceptor, Toll-like receptor 6, Transmembrane activator and CAML interactor (TACI), B cell maturation peptide (BCMA), CSF-1 receptor, Interferon (α, β and gamma) receptor 1 (IFNAR1). Pathways that can be modulated to increase antibody production include, e.g., ubiquitin/proteosome; telomerase; FGFR3; and Mcd-1, etc.

In certain embodiments of the disclosure, AVLP compositions can be utilized to prepare antigenic preparations that be used as vaccines. Any suitable antigen(s) can be prepared in accordance with the disclosure, including antigens obtained from prions, viruses, *mycobacterium*, protozoa (e.g., *Plasmodium falciparum* (malaria)), trypanosomes, bacteria (e.g., *Streptococcus, Neisseria*, etc.), etc.

Host cells can be transfected with single AVLP particles containing one or more heterologous polynucleotide sequences, or with a plurality of AVLP particles, where each comprises the same or different heterologous polynucleotide sequence(s). For example, a multi-subunit antigen (including intracellular and cell-surface multi-subunit components) can be prepared by expressing the individual subunits on separate vectors, but infecting the same host cell with all the vectors, such that assembly occurs within the host cell.

Vaccines often contain a plurality of antigen components, e.g., derived from different proteins, and/or from different epitopic regions of the same protein. For example, a vaccine against a viral disease can comprise one or more polypeptide sequences obtained from the virus which, when administered to a host, elicit an immunogenic or protective response to viral challenge.

As mentioned, the disclosure can also be utilized to prepare polypeptide multimers, e.g., where an antigenic preparation is produced which is comprised of more than one polypeptide. For instance, virus capsids can be made up of more than one polypeptide subunit. By transducing a host cell with vectors carrying different viral envelope sequences, the proteins, when expressed in the cell, can self-assemble into three-dimensional structures containing more than one protein subunit (e.g., in their native configuration).

In further embodiments, the expressible heterologous nucleotide sequence is derived from another virus, other than PIV5. For example, the heterologous nucleotide sequence may encode (from any strain) influenza HA, RSV F, HIV Gag and/or Env, etc. Such embodiments can be useful for developing vaccines and/or methods of vaccination. The examples given here are non-limiting, as it will be understand by those in the art that nucleotide sequences from a variety of pathogenic agents (including also bacteria, parasites, etc.) may be desirable to use for an AVLP vaccine composition and/or method of vaccination.

Examples of viruses to which vaccines can be produced in accordance with the disclosure include, e.g., orthomyxoviruses, influenza virus A (including all strains varying in their HA and NA proteins, such as (non-limiting examples) H1N1, H1N2, H2N2, H3N2, H7N7, and H3N8); influenza B, influenza C, thogoto virus (including Dhori, Batken virus, SiAR 126 virus), and isavirus (e.g., infectious salmon anemia virus), coronaviurses and the like. These include influenza isolated or transmitted from all species types, including isolates from invertebrates, vertebrates, mammals, humans, non-human primates, monkeys, pigs, cows, and other livestock, birds, domestic poultry such as turkeys, chickens, quail, and ducks, wild birds (including aquatic and terrestrial birds), reptiles, etc. These also include existing strains which have changed, e.g., through mutation, antigenic drift, antigenic shift, recombination, etc., especially strains which have increased virulence and/or interspecies transmission (e.g., human-to-human).

Of particular interest are influenza viruses which are panzootic and/or which cross species either because they have a broad host range, or because of recombination in the infected host, and/or because of naturally-occurring or directed mutation. For example, H5N1 (in reference to the subtypes of surface antigens present on the virus, hemagglutinin type 5 and neuraminadase type 1) is a subtype of avian influenza A, which caused an outbreak of flu in domestic birds in Asia. In one embodiment, the invented composition comprises a PIV5-based AVLP composition comprising an isolated polynucleotide as described herein which further comprises the HA sequence of H5N1.

An influenza antigenic preparation (such as a vaccine) can comprise one or more polypeptides that occur naturally in an influenza virion. However, it preferably does not comprise all the polypeptide genes that would give rise to the native pathogenic virus. These include, e.g., hemagglutinin (encoded by HA gene), neuraminidase (encoded by NA gene), nucleoprotein (encoded by NA gene), matrix (M1) proteins (encoded by M gene), M2 (encoded by M gene), non-structural proteins (encoded by NS gene), and polymerases. The naturally-occurring virion is sheathed in a lipid bilayer which is "studded" with integral proteins H and N ("capsid layer"). Matrix proteins (M1) form a protein layer ("matrix layer") underneath the viral membrane, and are involved in viral assembly, stability and integrity. See, e.g., Harris et al., Virol. 289:34-44, 2001. M2 protein is a membrane protein ion channel. AVLP of the disclosure can comprise H, N, and optionally M1 and M2 proteins. Sequences for said proteins are known in the art and/or can be identified in GenBank. See, e.g., Widjaja et al. J. Virol., 78:8771-8779, 2004 for M1 and M2 sequences. At least nine subtypes of H5 have been identified. H5 infections, such as HPAI H5N1 viruses currently circulating in Asia and Europe, have been documented among humans and can cause severe illness or death. At least nine subtypes of H7 have been identified. H7 infection in humans is rare but can occur among persons who have direct contact with infected birds. Symptoms may include conjunctivitis and/or upper respiratory symptoms. H7 viruses include, e.g., H7N2, H7N7, and H7N3), and have caused mild to severe and fatal illness in humans. The H subtypes are epidemiologically most important, as they govern the ability of the virus to bind to and enter cells, where multiplication of the virus then occurs. The N subtypes govern the release of newly formed virus from the cells. At least nine subtypes of H9 have been identified. Influenza A H9 has rarely been reported to infect humans. However there are reports of children exhibiting flu-like syndromes when infected with H9 strains.

The disclosure provides vaccines against all avian influenza subtypes (e.g., H and N subtypes), including existing subtypes, derivatives thereof, and recombinants thereof, such as subtypes and recombinants which have the ability to spread from human-to-human. Various isolates have been characterized, especially for H5 subtypes. See, e.g., Sturm-Ramirez, J. Virol., 2004, 78, 4892-4901; Guan et al., Proc. Natl. Acad. Sci., 2004, 101, 8156-8161.

The disclosure also provides methods for producing AVLP compositions. Examples of host cells which can be utilized to produce AVLP compositions, include, any mammalian or human cell line or primary cell. Non-limiting examples include, e.g., 293, HT1080, Jurkat, and SupT1 cells. Other examples are CHO, 293, Hela, Vero, L929, BHK, NIH 3T3, MRC-5, BAE-1, HEP-G2, NSO, U937, Namalwa, HL60, WEHI 231, YAC 1, U 266B1, SH-SY5Y, CHO, e.g., CHO-K1 (CCL-61), 293 (e.g., CRL-1573). Cells are cultured under conditions effective to produce transfection and expression. Such conditions include, e.g., the particular milieu needed to achieve protein production. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including cell media, substrates, oxygen, carbon dioxide, glucose and other sugar substrates, serum, growth factors, etc.).

The disclosure also provides various treatment methods involving delivering AVLP to host cells in vivo. In some embodiments, AVLP is delivered into a subject for treating or preventing cancer or a precancerous condition. In other embodiments, AVLP is delivered into a subject for treating or preventing diabetes. In further embodiments, AVLP is delivered into a subject for treating or preventing an inflammatory condition. In other embodiments, AVLP is delivered into a subject for treating or preventing an autoimmune condition. In some embodiments, AVLP is delivered into a subject for treating or preventing a transplantation-related condition. In yet other embodiments, AVLP is delivered into a subject for treating or preventing an infection (e.g., vaccination, as discussed further above and below in the examples).

In some embodiments encompassing methods of therapeutic use, the recipient subject has a disease selected from the group consisting of cancer, precancerous condition, autoimmune disease, inflammatory condition, transplant rejection, post-transplant lymphoproliferative disorder, allergic disorder, and infection.

Non-limiting examples of cancers treatable by the methods of the disclosure include, e.g., carcinomas, lymphomas, sarcomas, blastomas, and leukemias. Non-limiting specific examples, include, for example, breast cancer, pancreatic cancer, liver cancer, lung cancer, prostate cancer, colon cancer, renal cancer, bladder cancer, head and neck carcinoma, thyroid carcinoma, soft tissue sarcoma, ovarian cancer, primary or metastatic melanoma, squamous cell carcinoma, basal cell carcinoma, brain cancers of all histopathologic types, angiosarcoma, hemangiosarcoma, bone sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, testicular cancer, uterine cancer, cervical cancer, gastrointestinal cancer, mesothelioma, Ewing's tumor, leiomyosarcoma, Ewing's sarcoma, rhabdomyosarcoma, carcinoma of unknown primary (CUP), squamous cell carcinoma, basal cell carcinoma, adenocarcinoma, sweat gland carcinoma, sebaceous gland carcinoma, papillary carcinoma, Waldenstroom's macroglobulinemia, papillary adenocarcinomas, cystadenocarcinoma, bronchogenic carcinoma, bile duct carcinoma, choriocarcinoma, seminoma, embryonal carcinoma, Wilms' tumor, lung carcinoma, epithelial carcinoma, cervical cancer, testicular tumor, glioma, glioblastoma, astrocytoma, medulloblastoma, craniopharyngioma, ependymoma, pinealoma, hemangioblastoma, acoustic neuroma, oligodendroglioma, meningioma, retinoblastoma, leukemia, neuroblastoma, small cell lung carcinoma, bladder carcinoma, lymphoma, multiple myeloma, medullary carcinoma, B cell lymphoma, T cell lymphoma, NK cell lymphoma, large granular lymphocytic lymphoma or leukemia, gamma-delta T cell lymphoma or gamma-delta T cell leukemia, mantle cell lymphoma, myeloma, leukemia, chronic myeloid leukemia, acute myeloid leukemia, chronic lymphocytic leukemia, acute lymphocytic leukemia, hairy cell leukemia, hematopoietic neoplasias, thymoma, sarcoma, non-Hodgkin's lymphoma, Hodgkin's lymphoma, Epstein-Barr virus (EBV) induced malignancies of all types including but not limited to EBV-associated Hodkin's and non-Hodgkin's lymphoma, all forms of post-transplant lymphomas including post-transplant lymphoproliferative disorder (PTLD), uterine cancer, renal cell carcinoma, hepatoma, hepatoblastoma, etc.

Non-limiting examples of the inflammatory and autoimmune diseases treatable by the methods of the disclosure include, e.g., inflammatory bowel disease (IBD), ulcerative colitis (UC), Crohn's disease, diabetes (e.g., diabetes mellitus type 1), multiple sclerosis, arthritis (e.g., rheumatoid arthritis), Graves' disease, lupus erythematosus, ankylosing spondylitis, psoriasis, Behcet's disease, autistic enterocolitis, Guillain-Barre Syndrome, myasthenia gravis, pemphigus vulgaris, acute disseminated encephalomyelitis (ADEM), transverse myelitis autoimmune cardiomyopathy, Celiac disease, dermatomyositis, Wegener's granulomatosis, allergy, asthma, contact dermatitis, atherosclerosis (or any other inflammatory condition affecting the heart or vascular system), autoimmune uveitis, as well as other autoimmune skin conditions, autoimmune kidney, lung, or liver conditions, autoimmune neuropathies, etc.

In some embodiments, AVLP can be modified or engineered to contain polypeptide sequences that allow the transduction vector to target and infect host cells outside its normal range or more specifically limit transduction to a cell or tissue type. For example, receptor ligands, antibodies (using an antigen-binding portion of an antibody or a recombinant antibody-type molecule, such as a single chain antibody), and polypeptide moieties or modifications thereof (e.g., where a glycosylation site is present in the targeting sequence) may be used that, facilitate directed delivery of the AVLP system to a target cell of interest. For example, in addition to F and HN, other glycoproteins can be used to generate particles from AVLP-infected cells. If targeting specific cell type is required, AVLP can be pseudotyped by other proteins, such as, for example (VSV-G pseudotyped AVLP-EGFP).

In yet other embodiments, AVLP is delivered into a subject for treating or preventing an infection. The infections treatable by the methods of the disclosure include, without limitation, those which can be caused by, for example, a bacterium, parasite, virus, fungus, or protozoa.

It is contemplated that when used to treat various diseases, the compositions and methods of the disclosure can be combined with other therapeutic agents suitable for the same or similar diseases. Also, two or more embodiments of the disclosure may be also co-administered to generate additive or synergistic effects. When co-administered with a second therapeutic agent, the embodiment of the disclosure and the second therapeutic agent may be simultaneously or sequentially (in any order). Suitable therapeutically effective dosages for each agent may be lowered due to the additive action or synergy.

As a non-limiting example, the disclosure can be combined with other therapies that block inflammation through (e.g., via inhibition, reduction and/or blockage of IL1, INF$\alpha/\beta$, IL6, TNF, L13, IL23, etc.). In some embodiments, AVLP compositions and methods disclosed herein are useful to enhance the efficacy of vaccines directed to tumors or infections. The compositions and methods of the disclosure can be administered to a subject either simultaneously with or before (e.g., 1-30 days before) a reagent (including but not limited to small molecules, antibodies, or cellular reagents) that acts to elicit an immune response (e.g., to treat cancer or an infection). The compositions and methods of the disclosure can be also administered in combination with an anti-tumor antibody or an antibody directed at a pathogenic antigen or allergen.

The compositions and methods of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.). The inhibitory treatments of the disclosure can be also combined with other treatments that possess the ability to modulate gene expression.

Therapeutic methods of the disclosure can be combined with additional therapies. For example, when used for treating cancer, AVLP can be used in combination with conventional cancer therapies, such as, e.g., surgery, radiotherapy, chemotherapy or combinations thereof, depending on type of the tumor, patient condition, other health issues, and a variety of factors.

Other therapeutic agents useful for combination cancer therapy with AVLP include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the inhibitors of the disclosure can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the disclosure include, e.g., aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, e.g., following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate), platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

For treatment of infections, combined therapy with AVLP can encompass co-administering compositions and methods of the disclosure with, e.g., an antibiotic, an anti-fungal drug, an anti-viral drug, an anti-parasitic drug, an anti-protozoal drug, or a combination thereof.

Non-limiting examples of useful antibiotics include lincosamides (clindomycin); chloramphenicols; tetracyclines (such as Tetracycline, Chlortetracycline, Demeclocycline, Methacycline, Doxycycline, Minocycline); aminoglycosides (such as Gentamicin, Tobramycin, Netilmicin, Amikacin, Kanamycin, Streptomycin, Neomycin); beta-lactams (such as penicillins, cephalosporins, Imipenem, Aztreonam); vancomycins; bacitracins; macrolides (erythromycins), amphotericins; sulfonamides (such as Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole); Methenamin; Nitrofurantoin; Phenazopyridine; trimethoprim; rifampicins; metronidazoles; cefazolins; Lincomycin; Spectinomycin; mupirocins; quinolones (such as Nalidixic Acid, Cinoxacin, Norfloxacin, Ciprofloxacin, Perfloxacin, Ofloxacin, Enoxacin, Fleroxacin, Levofloxacin); novobiocins; polymixins; gramicidins; and antipseudomonals (such as Carbenicillin, Carbenicillin Indanyl, Ticarcillin, Azlocillin, Mezlocillin, Piperacillin) or any salts or variants thereof. See also Physician's Desk Reference (2005), Thomson P D R, Montvale N.J.; Gennaro et al., Eds. Remington's The Science and Practice of Pharmacy (2000), Lippincott Williams and Wilkins, Baltimore Md.; Braunwald et al., Eds. Harrison's Principles of Internal Medicine, (2001), McGraw Hill, NY; Berkow et al., Eds. The Merck Manual of Diagnosis and Therapy (1992), Merck Research Laboratories, Rahway N.J. Antibiotics can be obtained commercially, e.g., from Daiichi Sankyo, Inc. (Parsippany, N.J.), Merck (Whitehouse Station, N.J.), Pfizer (New York, N.Y.), Glaxo Smith Kline (Research Triangle Park, N.C.), Johnson & Johnson (New Brunswick, N.J.), AstraZeneca (Wilmington, Del.), Novartis (East Hanover, N.J.), and Sanofi-Aventis (Bridgewater, N.J.). The antibiotic used will depend on the type of infection.

Non-limiting examples of useful anti-fungal agents include, e.g., imidazoles (such as griseofulvin, miconazole, terbinafine, fluconazole, ketoconazole, voriconazole, and itraconizole); polyenes (such as amphotericin B and nystatin); Flucytosines; and candicidin or any salts or variants thereof. See also Physician's Desk Reference (2005), Thomson P D R, Montvale N.J.; Gennaro et al., Eds. Remington's The Science and Practice of Pharmacy (2000), Lippincott Williams and Wilkins, Baltimore Md.; Braunwald et al., Eds. Harrison's Principles of Internal Medicine (2001), McGraw Hill, NY; Berkow et al., Eds. The Merck Manual of Diagnosis and Therapy (1992), Merck Research Laboratories, Rahway N.J.

Non-limiting examples of useful anti-viral drugs include, e.g., interferon alpha, beta or gamma, didanosine, lamivudine, zanamavir, lopanivir, nelfinavir, efavirenz, indinavir, valacyclovir, zidovudine, amantadine, rimantidine, ribavirin, ganciclovir, foscarnet, and acyclovir or any salts or variants thereof. See also Physician's Desk Reference (2005), Thomson P D R, Montvale N.J.; Gennaro et al., Eds. Remington's The Science and Practice of Pharmacy (2000), Lippincott Williams and Wilkins, Baltimore Md.; Braunwald et al., Eds. Harrison's Principles of Internal Medicine (2001), McGraw Hill, NY; Berkow et al., Eds. The Merck Manual of Diagnosis and Therapy (1992), Merck Research Laboratories, Rahway N.J.

Non-limiting examples of useful anti-parasitic agents include, e.g., chloroquine, mefloquine, quinine, primaquine, atovaquone, sulfasoxine, and pyrimethamine or any salts or variants thereof. See also Physician's Desk Reference (2005), Thomson P D R, Montvale N.J.; Gennaro et al., Eds. Remington's The Science and Practice of Pharmacy (2000), Lippincott Williams and Wilkins, Baltimore Md.; Braunwald et al., Eds. Harrison's Principles of Internal Medicine (2001), McGraw Hill, NY; Berkow et al., Eds. The Merck Manual of Diagnosis and Therapy (1992), Merck Research Laboratories, Rahway N.J.

Non-limiting examples of useful anti-protozoal drugs include, e.g., metronidazole, diloxanide, iodoquinol, trimethoprim, sufamethoxazole, pentamidine, clindamycin, primaquine, pyrimethamine, and sulfadiazine or any salts or variants thereof. See also Physician's Desk Reference, 59 edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15th edition, (2001), McGraw Hill, NY; Berkow et al., Eds. The Merck Manual of Diagnosis and Therapy, (1992), Merck Research Laboratories, Rahway N.J.

EXAMPLES

The disclosure is also described and demonstrated by way of the following examples. The use of these and other examples anywhere in the specification is illustrative only and in no way limits the scope and meaning of the disclosure or of any exemplified term. Likewise, the disclosure is not limited to any particular preferred embodiments described here.

Many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1

The disclosure will be further understood by those of skill in the art by reference to the below exemplary, non-limiting embodiments:

For cell culture, BHK21, Vero and HeLa cells were maintained in Dulbecco's modified Eagle medium (DMEM) with 10% fetal bovine serum (FBS) and 1% penicillin-streptomycin. MDBK cells are grown in DMEM with 10% FBS. Hygromycin was added to the medium of BHK21 and Vero cell lines to make final concentration of 50 to 500 Jpg/mL. For PIV5 virus infection, the monolayers were washed with phosphate-buffered saline (PBS) and then inoculate with virus in DMEM plus 1% bovine serum albumin. The monolayers were washed again with PBS and incubate with DMEM containing 2% FBS at 37° C. with 5% $CO_2$.

For PIV5 starting material, PIV5-H5/SH-HN (ZL46) was used (described by Li, Z. et al. Recombinant Parainfluenza Virus 5 Expressing Hemagglutinin of Influenza A Virus H5N1 Protected Mice against Lethal Highly Pathogenic Avian Influenza Virus H5N1 Challenge 2013 J. Virol.). Other PIV5 strains are also contemplated.

To concentrate PIV5 or AVLP-H5 virus particles, the supernatants containing virus were loaded onto 20% sucrose and pelleted in a Thermo scientific ultracentrifuge Type F40L-8×100 rotor at 37,000 rpm for 1 h. Resulting pellets were resuspended in PBS with 1% BSA and store at −80° C.

Highly pathogenic A/Vietnam/1203/2004 (H5N1; provided by Richard Webby, St. Jude Children's Research Hospital, Memphis, Tenn.) were propagated in the allantoic cavity of embryonated hen eggs at 37° C. for 24 hr, and then divided into aliquots and store at −80° C. All experiments using live, highly pathogenic A/Vietnam/1203/2004 should be conducted in at least enhanced biosafety level 3 (BSL3+) containment, according to guidelines for the use of select agents approved by the CDC.

To generate a plasmid containing PIV5 AVLP (pAVLP), the infectious clone plasmid pPIV5 containing the full-length genome of PIV5 was used (virus described by Cornwell H J, McCandlish I A, Thompson H, Laird H M, Wright N G. 1976. Isolation of parainfluenza virus SV5 from dogs with respiratory disease. Vet Rec 98:301-302). The PIV5 F, HN, and SH genes were deleted and a selection marker gene, Hygromycin, was introduced between V/P and L genes. As described further herein, the expressible heterologous nucleotide sequence of interest (e.g., EGFP or H5N1 HA) was inserted into the pAVLP between V/P and Hygromycin genes to obtain pAVLP-EGFP or pAVLP-H5. The length of PIV5 AVLP genome should be maintained as a multiple of six.

To establish stable cell lines carrying PIV5 AVLP genome and initiate the transcription and replication of PIV5 virus AVLP genome in the cells, the plasmid pAVLP-EGFP or H5(3 µg), along with plasmids pCAGGS-PIV5-L (1.5 µg), pCAGGS-PIV5-NP (1 g), pCAGGS-PIV5-P (200 ng), and pBH437 (expressing T7 polymerase, 500 ng) were transfected into BHK21 cells in a 6-well plate. At 4 to 6 hours post-transfection, the medium was removed and replaced with fresh medium. The Hygromycin was added at 2 to 4 days post-transfection. Through selection by hygromycin for 2 to 5 weeks, the surviving cells were developed into BHK21 cell lines carrying PIV5 AVLP genome.

To get the single-cycle infectious PIV5 AVLP particles (AVLP), the plasmids expressing PIV5 F, HN, and M at a ratio of 2:1:1 were transfected into stable cell lines carrying PIV5 AVLP genome. The supernatants were collected at 2 to 3 days post-transfection. The cell debris was removed by low speed centrifugation or by 0.44 µm filters. The cleared supernatants containing AVLP may be used to infect fresh cells for determination of protein expression levels or development of additional cell lines.

To investigate the stability of PIV5 AVLP genome in the cells, the AVLP genomic RNA was extracted from the cells using RNeasy Mini Kit (QIAGEN), and perform reverse transcription (RT) with PIV5 gene specific primers. The reverse transcription product was further amplified by PCR using specific primers covering whole PIV5 AVLP genome, then the PCR products were sequenced by any standard method.

To detect expression of the PIV5 or H5 proteins, AVLP infected cells or cell lines carrying PIV5 AVLP genome were examined by indirect immunofluorescence assay (IFA) (as described by Lin Y, Horvath F, Aligo J A, Wilson R, He B. 2005. The role of simian virus 5 V protein on viral RNA synthesis. Virology 338:270-280). To do this, cells were fixed with 3.7% formaldehyde in PBS (pH 7.4) for 10 min, and then treated with 0.1% Triton X-100 plus 1% BSA, or 1% BSA in PBS for 30 min at room temperature. Fixed cells were incubated for 1 h with primary antibody at 37° C. and then incubated with FITC-conjugated secondary antibody. The cells were further washed and placed on slides. ProLong® Gold Antifade Mountant (Life Technologies) was applied directly to fluorescently labeled cells and coverslips were added. Fluorescence was examined and photographed using a Nikon FXA fluorescence microscope and a Zeiss 410 confocal microscope.

Further detection was performed by western blotting. To do this, cells carrying PIV5 AVLP genome were lysed with whole-cell extraction buffer (WCEB) (50 mM Tris-HCl [pH 8], 280 mM NaCl, 0.5% NP-40, 0.2 mM EDTA, 2 mM EGTA, and 10% glycerol). The lysates were cleared by centrifugation at 4000 rpm for 15 minutes and the supernatants were mixed with the same volume of 2×SDS loading buffer (100 mM Tris-HCl [pH 6.8], 20% glycerol, 4% SDS, 200 mM dithiothreitol [DTT], and 0.1% bromophenol blue), heated at 95° C. for 5 min, and resolved by 10% SDS-PAGE. The proteins were transferred onto a polyvinylidene difluoride (PVDF) membrane using an iBlot dry blotting system (Invitrogen). The membrane was incubated with mouse anti-H5 antibody (1:2000 dilution), mouse anti-PIV5-V/P, or mouse anti-PIV5-NP antibody (1:2000 dilution), followed by incubation with goat anti-mouse secondary antibody labeled with horseradish peroxidase (HRP) at dilution of 1:2000. After washing, the PVDF membrane was incubated with ECL Advance Substrate (GE Healthcare) and scan using a Kodak Image Station 440.

To examine AVLP particles, the particles were loaded in the cleared supernatant onto 20% sucrose and pelleted in a Thermo scientific ultracentrifuge Type F40L-8×100 rotor at 37,000 rpm for 1 h. The pellets were then resuspended in phosphate buffered saline (PBS) buffer (pH 7.4). Purified PIV5 or AVLP particles were absorbed onto Parlodion-coated nickel grids for 30 s. The grids were floated on a drop of Tris-buffered saline (TBS), pH 7.4, for 5 min, followed by floating on drops of 3% ovalbumin in TBS for 1 h with PIV5 HN-specific mouse monoclonal antibody diluted to 1:300 in 1% ovalbumin in TBS. After washing with TBS three times, samples were incubated for 1 h with goat anti-mouse IgG coupled to 10-nm gold particles diluted at 1:10 in 1% ovalbumin in TBS. The grids were washed again with TBS and then stained with 2% phosphotungstic acid, pH 6.6. The grids were examined using a JEOL 1230 transmission electron microscope (JEOL, Tokyo, Japan).

Six- to 8-week-old female BALB/c mice were used in the animal studies. All animal experiments were performed following protocols approved by an Institutional Animal Care and Use Committee. The mouse immunization was performed by the intranasal (i.n.) route. For intranasal immunization, 6-week-old BALB/c mice were anesthetized by intraperitoneal injection of tribromoethanol (Avertin; 180 to 250 μl/kg of body weight) and then inoculated intranasally by dropping 100 μl AVLP or PIV5-H5/SH-HN at a dose of $2\times10^4$ PFU. PBS-treated mice served as controls. 19 days later, the mice in the AVLP-H5 vaccinated group were boosted with the same dose as the first inoculation. Mouse blood samples were collected by submandibular bleeding 6 days prior to challenge for serological assessment.

The mouse challenge was carried out at 42 days after prime immunization for the groups with one dose of PBS or PIV5-H5/SH-HN or the group with two doses of AVLP-H5. Anesthetized mice were inoculated intranasally with 10 50% lethal infectious doses (LD50) A/Vietnam/1203/04 diluted in 50 μl PBS. Mice were monitored daily for morbidity and mortality. Body weights were measured every other day.

H5 antigen-specific IgG antibody titers were measured by ELISA. Immulon® 2HB 96-well microtiter plates were coated with 100 μL of purified H5 protein at 1 μg/mL in PBS and incubated overnight at 4° C. Two-fold serial dilutions of serum were made in blocking buffer (1% BSA in wash buffer; KPL, Inc., Gaithersburg, Md., USA). 100 μL of each dilution were transferred to the plates and incubated for two hours at room temperature. After aspirating the samples, the plates were washed three times with wash buffer. The secondary antibody was diluted 1:2000 [horseradish-peroxidase-labeled goat anti-IgG (SouthernBiotech, Birmingham, Ala., USA)] in blocking buffer. 100 μL of diluted secondary antibody were added to each well, and the plates were incubated for 1 h at room temperature. After aspiration, the plates were washed and developed with 100 μL of SureBlue Reserve TMB substrate (KPL, Inc.) at room temperature. The OD at 450 nm was read using a BioTek Epoch microplate reader. The endpoint antibody titer was defined as the highest serum dilution at which the OD is greater than two standard deviations above the mean OD of the naïve serum.

A hemagglutination inhibition (HAI) assay was performed according to the WHO Manual on Animal Influenza Diagnosis and Surveillance. Chicken red blood cells (cRBCs) were washed and suspended to a final concentration of 0.5% in PBS. The inactivated influenza A virus (A/Vietnam/1203/04) was adjusted to 4 hemagglutination units (HAU) per 25 μl in PBS. In 96-well round-bottom plates, 25 μl of individual RDE-treated serum samples were serially diluted in a two-fold manner. After preparing serial dilution of sera, 25 μl (4 HAU) of the diluted virus were added. The plate was gently mixed and incubated at room temperature for 1 h. Then 50 ul of 0.5% cRBCs were added to each well, gently mixed, and incubated at room temperature for 30 to 45 minutes. Hemagglutination was scored by tilting the plate at a 45 degree angle. The HAI titer is the reciprocal of the last dilution antiserum that completely inhibits hemagglutination.

Enzyme-linked immunosorbent spot (ELISpot) assay was performed to detect T-cell responses in lymphocytes to influenza virus H5N1 HA antigen. Cells were stimulated with 0.1 μg of influenza virus H5N1 HA antigen, with 0.1 μg of Tuberculosis E6 protein as an irrelevant antigen, or with phorbol myristate acetate-ionomycin in 50 μl complete tumor medium (CTM). Spots were counted using an AID ViruSpot Reader (Cell Technology, Inc.). The results were presented as mean numbers of cytokine-secreting cells subtracted from the total number of mock-stimulated cells per $10^6$ splenocytes.

Difference comparisons (i.e., data analysis) were made using Student t test within the program GraphPad Prism 5.0

(GraphPad Software, San Diego, Calif., USA). Differences were considered statistically significant when P was <0.05 and most significant when P<0.01.

Example 2

The disclosure will be further understood by those of skill in the art by reference to the below exemplary, non-limiting embodiments:

To generate AVLP-EGFP, plasmid containing PIV5 genes NP, V/P and L that encodes NP, P and L respectively with regulatory sequences (leader, trailer and appropriate gene junctions sequences) was provided (FIG. 1A). M, F, SH and HN of PIV5 were deleted from the full-length genome of PIV5. EGFP was chosen as a reporter for tracking of live cells and insert the EGFP gene downstream of the V/P gene. To allow selection of cells containing AVLP, a selection marker, hygromycin resistant gene (Hyg), was inserted in the AVLP (FIG. 1A).

The plasmid pAVLP-EGFP was transfected with plasmids pCAGGS-PIV5-L, pCAGGS-PIV5-NP, pCAGGS-PIV5-P, and pBH437 (expressing T7 RNA polymerase) into BHK21 cells. Transfected cells were passed and selected in hygromycin for 2 to 3 weeks. Individual colonies of selected cells were expanded (FIG. 1B). The green fluorescence signals were found in cells as early as two weeks (FIG. 1C).

Similarly, Vero cells containing AVLP-EGFP were generated (FIG. 1C). Expression of PIV5 proteins was examined using immunoblotting with antibodies specific for PIV5 NP and P (FIG. 1D). NP and P of PIV5 were detected in these cells. Furthermore, RNAs were purified from the cells and AVLP genomes in these cells were sequenced using RT-PCR sequencing. The AVLP RNA sequences should generally match to the input cDNA sequence in plasmid pAVLP-EGFP.

To obtain particles from the cells containing AVLP-EGFP genome, the cells were transfected with the plasmids expressing PIV5 F, HN, and M (FIG. 1B). The supernatants containing single-cycle infectious PIV5 particles (AVLP-EGFP) were filtered. The cleaned supernatants of the transfected cells were used to "infect" fresh HeLa cells (i.e., these cells had not encountered AVLP-EGFP before).

For reference, FIG. 1A shows schematics of PIV5, AVLP-EGFP, and AVLP-H5. NP, nucleoprotein; P, phosphoprotein; V, V protein; M, matrix protein; SH, small hydrophobic protein; F, fusion protein; HN, Hemagglutinin-neuraminidase protein; L, RNA-dependent RNA polymerase; Hyg, Hygromycin; EGFP, Enhanced Green Fluorescent Protein; H5, influenza virus A H5N1 HA.

For further reference, FIG. 1B shows schematics of AVLP generation. Cells were transfected with plasmids expressing PIV5 P, NP, L and T7 polymerase together with PIV5 AVLP plasmid expressing EGFP. The transfected cells were selected with hygromycin. BHK21 (AVLP-EGFP) cell clones containing PIV5 AVLP genome and expressing Hygromycin were expanded under selection of Hygromycin. BHK21 (AVLP-EGFP) cells were transfected with plasmids expressing PIV5 F, HN and M. Particles carrying PIV5 AVLP genome packaged by PIV5 HN, F, and M were generated in the supernatants of transfected cells. The particles were designated as AVLP-EGFP and used to infect Vero cells. The infected Vero cells were developed into cell lines carrying PIV5 AVLP genome (Vero(AVLP-EGFP)) under selection of Hygromycin. Vero (AVLP-EGFP) cells were transfected with plasmids expressing PIV5 F, HN and M, and then AVLP-EGFP particles are produced in the supernatants of transfected cells.

For further reference, FIG. 1C shows detection of EGFP expression using fluorescence microscopy. EGFP expression in stable BHK21 and Vero cell lines were identified by fluorescence microscopy. In addition, FIG. 1D shows detection of PIV5 V/P and NP expression using western blotting (WB). PIV5 V/P and NP expression was examined in BHK21 (AVLP-EGFP) and Vero (AVLP-EGFP) by WB using mouse anti-PIV5 V/P and NP antibodies with BHK21 and Vero cells as negative control.

As shown in FIG. 2A, expression of EGFP was observed in HeLa cells up to 7 days post-inoculation with the media from the cells containing AVLP-EGFP genome, indicating infectious AVLP-EGFP. Similarly, expression of EGFP was detected in Vero cells up to 11 days post-inoculation with the media (FIG. 2B).

For reference FIG. 2, shows HeLa (FIG. 2A) and Vero (FIG. 2B) cells infected by filtered supernatants containing AVLP-EGFP. The images were taken at 2, 7 and 11 days post infection using a fluorescence microscope.

The numbers of infectious particle in media were determined by counting numbers of cells showing GFP at 1 day post-inoculation and titers of AVLP were found to be over $10^6$ infectious particles per milliliter (IP/mL). In the absence of selection pressure (i.e., no hygromycin in the media) the cells should be able to be passed for at least three generations without obvious loss of AVLP-EGFP in progeny cells.

Example 3

The disclosure will be further understood by those of skill in the art by reference to the below exemplary, non-limiting embodiments:

AVLP-EGFP from Example 2 can be used as starting material to generate variants (e.g., AVLP-H5). However, new PIV5 starting material may also be used as desired, by following the disclosure given above and replacing EGFP with another expressible heterologous nucleotide sequence of interest (e.g., influenza H5N1 HA).

For example, to generate AVLP expressing HA of H5N1 (AVLP-H5), EGFP in AVLP-EGFP plasmid was replaced with HA of H5N1 (H5). As exemplified here, the H5 is the same as the one described in the full-length PIV5 genome (ZL46), in which the polybasic cleavage site of H5 is removed.

AVLP-H5 was obtained as similarly described for AVLP-EGFP (FIG. 1A and FIG. 3). For example, AVLP-H5 particles were obtained from supernatants of Vero (AVLP-H5) cells transfected with plasmids encoding PIV5 F, HN and M. The titer of AVLP-H5 infectious particles was about $4 \times 10^6$ IP/mL. The H5 protein was detectable in AVLP-H5 and PIV5-H5/SH-HN infected Vero cells, and mainly localized on the cell membrane (FIG. 4).

For reference, FIG. 3A shows identification of H5 and PIV5 V/P expression in the Vero (AVLP-H5) cells by IFA. The Vero (AVLP-H5) cells were fixed and stained with anti-H5 or anti-PIV5 V/P antibodies followed by staining with FITC-conjugated secondary antibody. DAPI staining was performed after ProLong® Gold Antifade Mountant is applied to the cell samples. FIG. 3B shows identification of H5, PIV5 V/P and NP expression in the Vero (AVLP-H5) cells by western blotting. The Vero (AVLP-H5) cell samples were stained with anti-H5, anti-PIV5 V/P, or anti-PIV5 NP antibodies, and Vero cell samples were used as negative control.

Figure 4:
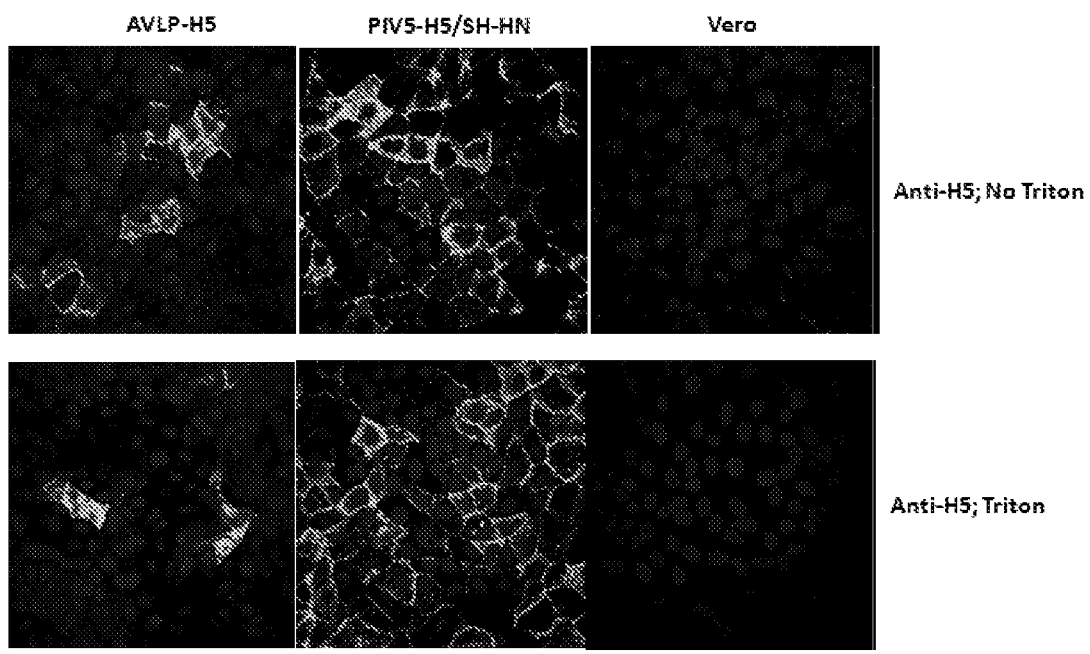
FIG. 4 shows the characterization of H5 expression in Vero cells infected with AVLP-H5 or PIV5-H5/S well as the disease and its severity and the age, weight, physical condition and responsiveness of the mammal to be treated.

For further reference, FIG. 4 shows Vero cells infected with AVLP-H5 or PIV5-H5/SH-HN. Two days later, Vero cells were fixed and treated with triton or PBS. The cells were stained with anti-H5 antibody followed by staining with FITC-conjugated secondary antibody. DAPI staining was performed after ProLong® Gold Antifade Mountant was applied to the cell samples.

Using EM analysis, the AVLP-H5 particles were stained by anti-PIV5 HN antibody. AVLP-H5 should be similar in sizes and shapes to the wild-type PIV5 particles and H5 should not be detectable in the AVLP-H5 using anti-H5 antibody (FIG. 5).

Figure 5:
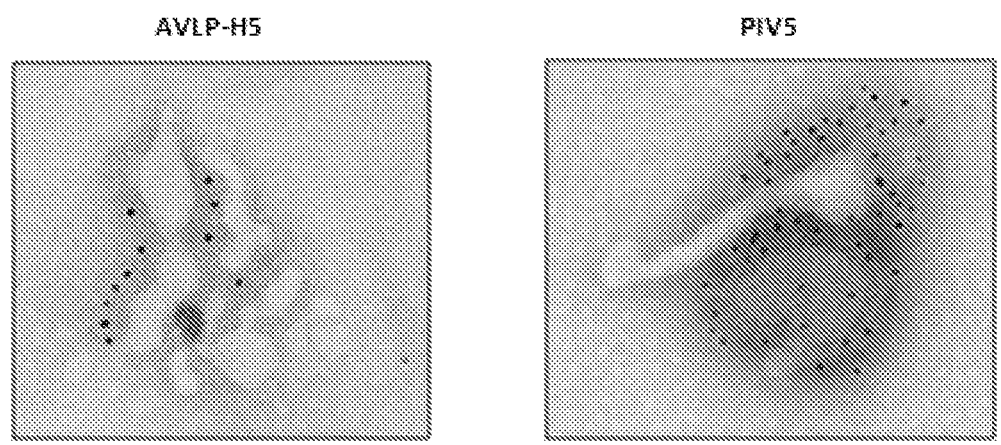

For reference, FIG. 5 shows the purified AVLP-H5 and PIV5 particles treated with anti-PIV5 HN antibody and then secondary antibody labeled with gold particles. The samples were examined using an electron microscope.

To investigate HA antibody production in vivo, mice were vaccinated with PBS, a PIV5 expressing H5 (PIV5-H5/SH-HN; as described in Li Z, Mooney A J, Gabbard J D, Gao X, Xu P, Place R J, Hogan R J, Tompkins S M, He B. 2013. Recombinant Parainfluenza Virus 5 Expressing Hemagglutinin of Influenza A Virus H5N1 Protected Mice against Lethal Highly Pathogenic Avian Influenza Virus H5N1 Challenge. Journal of virology 87:354-362), and AVLP-H5 intranasally. For AVLP-H5, a boost at was performed 19 days after initial immunization. At 26 days after initial immunization, blood samples were collected and sera were prepared. Two doses of AVLP-H5 and one dose of PIV5-H5/SH-HN vaccination induced specific anti-H5-HA antibodies. AVLP-H5-vaccinated mice induced higher levels of ELISA antibody than PIV5-H5-vaccinated mice.

A HAI titer assay was performed with serum samples. Here, six of eight AVLP-H5-immunized mice showed detectable HAI titers between the range of 10 to 40, while six of seven PIV5-H5/SH-HN vaccinated mice had HAI titers from 10 to 40. No HAI was detected in mice in the PBS group.

Cellular immune responses induced by PIV5-H5 and AVLP-H5 were examined using an IFN-γ ELISPOT assay. At 26 days after initial immunization, mice were euthanized and splenocytes for IFN-γ ELISPOT assays were obtained. Compared to PBS control mice, PIV5-H5 and AVLP-H5-vaccinated mice induced specific and comparable levels of H5-specific cellular immune responses.

Figure 6:
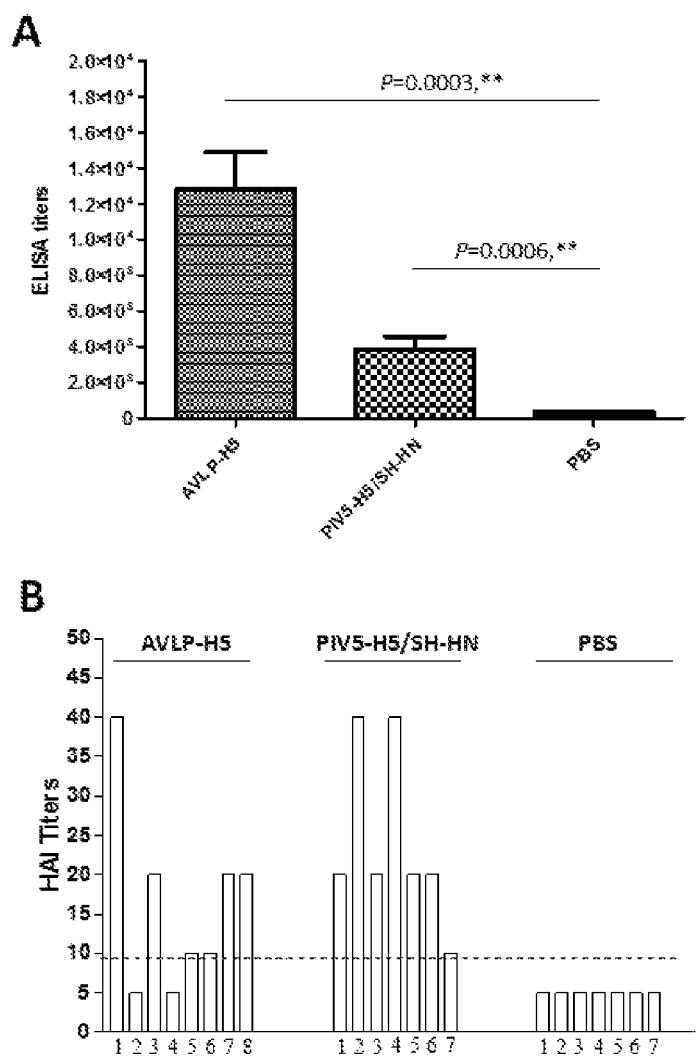

For reference, FIG. 6A shows ELISA titers of anti-H5 antibodies in mice. BALB/c mice were intranasally immunized with AVLP-H5 or PIV5-H5/SH-HN and bled on day 26 post prime immunization. The mouse blood samples were collected for analysis. HA (H5)-specific antibody titers were measured in serum samples using an IgG-specific ELISA. Differences were evaluated by Student's t test. (**, $P<0.01$). Whereas FIG. 6B shows HAI titers of anti-H5 antibodies in mice. 4 HAU of the influenza A virus (A/Vietnam/1203/04) were mixed with serially diluted mouse sera in 96-well round-bottom plates. The hemagglutination inhibition (HAI) titer is scored as the reciprocal of the highest dilution antiserum that completely inhibits hemagglutination. The graph shows the mean value of duplicate wells for each mouse. The limit of detection of the HAI titer (10) is indicated by dash line.

It was then determined whether AVLP-H5 particle vaccine can provide protection against H5N1 challenge. Immunized mice were challenged with 10 $LD_{50}$ H5N1 at 32 days after initial immunization. All PBS-immunized mice lost body weight and succumbed to the infection. In contrast, 100% of mice vaccinated with PIV5-H5/SH-HN (here, 10/10 mice) and AVLP-H5 (here, 15/15 mice) survived the challenge, indicating that AVLP-H5 immunization provided robust and comparable protection.

Figure 7:
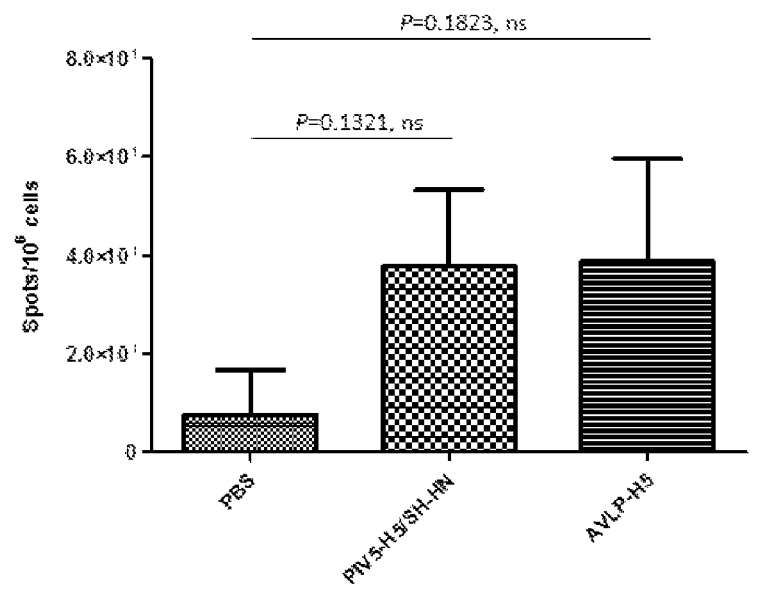

For reference, mice in FIG. 7 were vaccinated with a single dose of PBS or PIV5-H5/SH-HN, or two doses of AVLP-H5 intranasally (n=5 per group). At day 26 post-prime immunization, mice were sacrificed, and spleens collected. Splenocytes were stimulated with H5. Results are presented as the mean number of IFN-γ-producing cells per $10^6$ splenocytes. Differences are evaluated by Student's t test. (*, $P<0.05$; ns, not significant).

Figure 8:
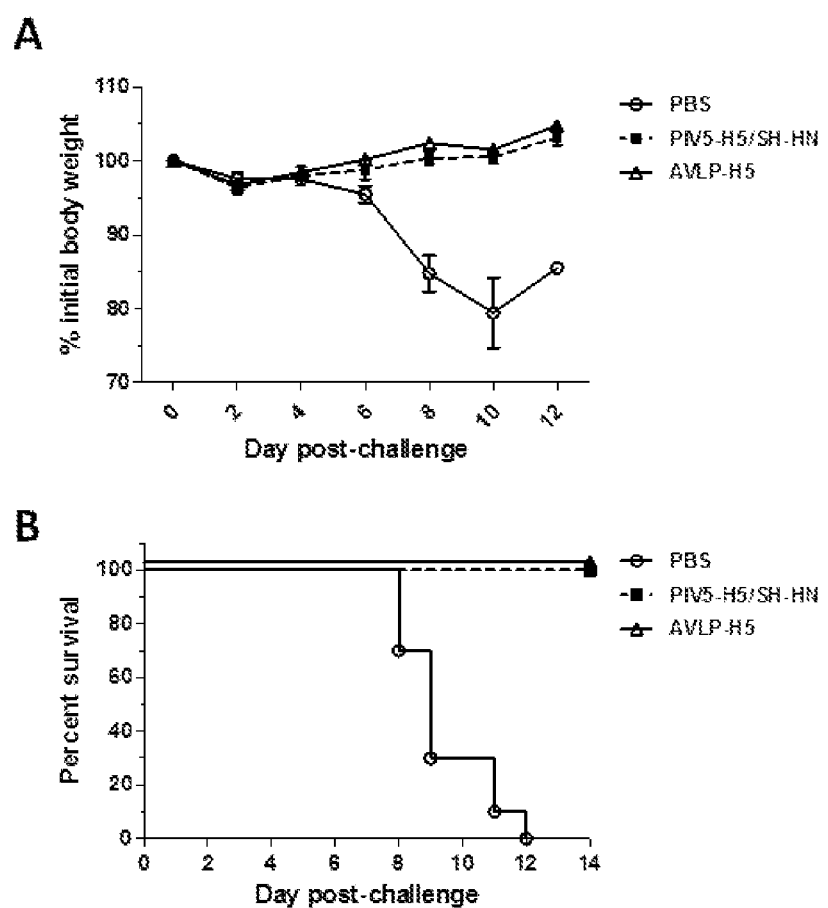

For further reference, mice in FIG. 8 were vaccinated with a single dose of PBS or PIV5-H5/SH-HN (n=10 per group), or two doses of AVLP-H5 intranasally (n=15 per group). At day 32 post prime vaccination, mice were challenged with 10 $LD_{50}$ of H5N1 influenza A virus (A/Vietnam/1203/04). Weight loss (shown in FIG. 8A) and survival (shown in FIG. 8B) were monitored at two days interval for 14 days following influenza virus challenge. Weight loss is graphed as an average percentage of the original weight (the day of challenge).

This exemplary embodiment demonstrates AVLP variants can be generated and used as a platform to deliver expressible heterologous nucleotide sequences of interest, which can have therapeutic applications such as here, e.g., vaccination against influenza H5N1. Those of skill in the art will recognize that additional AVLP variants can be generated using variations of the above approach, and employed to treat and/or prevent certain human and animal diseases.

Example 4

Figure 19:
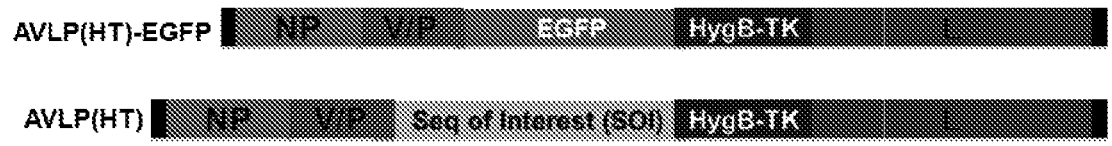

The disclosure will be further understood by those of skill in the art by reference to the below exemplary, non-limiting embodiments:

AVLP containing a hygromycin (Hyg)-thymidine kinase (TK) fusion protein in place of Hyg (FIG. 19) responds to administration of a positive selection stimuli (e.g., hygromycin) or a negative selection stimuli (e.g., acyclovir (ATC: J05AB01) or ganciclovir (ATC: J05AB06).)

Figure 25:
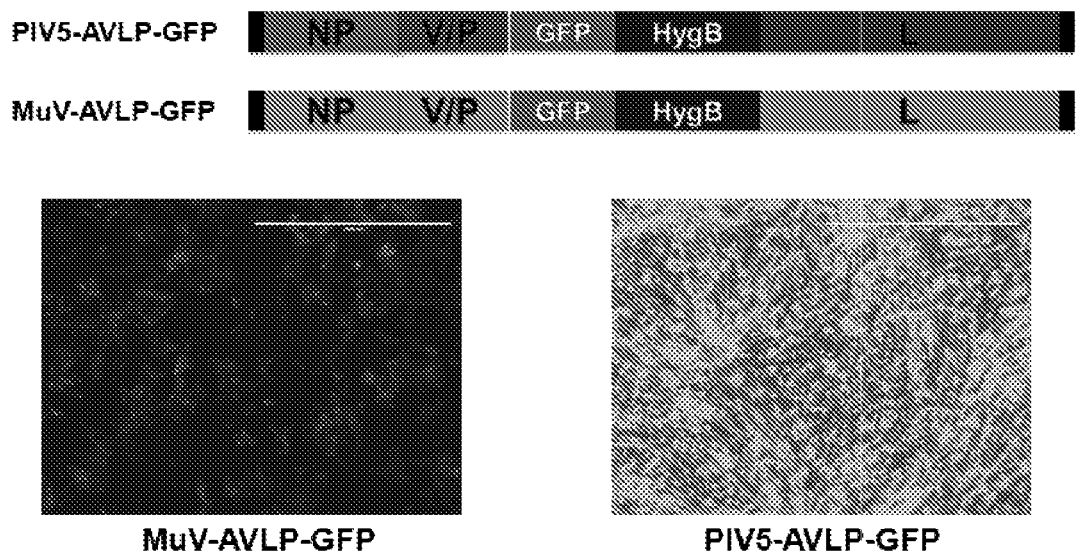

AVLP-Hyg-TK allowed expression of sequences of interest by positive selection with hygromycin selection, or killinvg of cells with sequences of interest with acyclovir (ATC: J05AB01) or ganciclovir (ATC: J05AB06) (FIG. 25). This AVLP variant is capable of use in multiple applications—for example, gene therapy, cancer therapy and/or vaccine development—and can be switched off at will. It is also possible to express TK by itself, or fuse it with other viral proteins such as NP, V/P or L within the AVLP system. Other so-called "suicide gene" systems (e.g., tomato thymidine kinase and AZT) may also be used.

Example 5

Figure 20:
Figure 23:
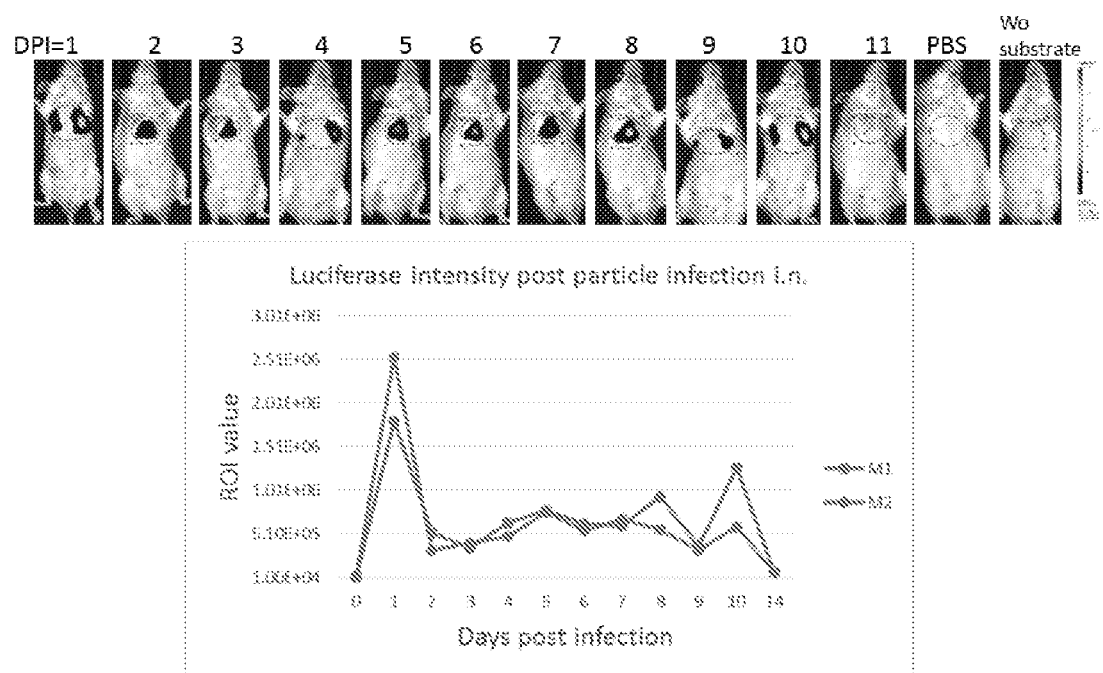
Figure 24:
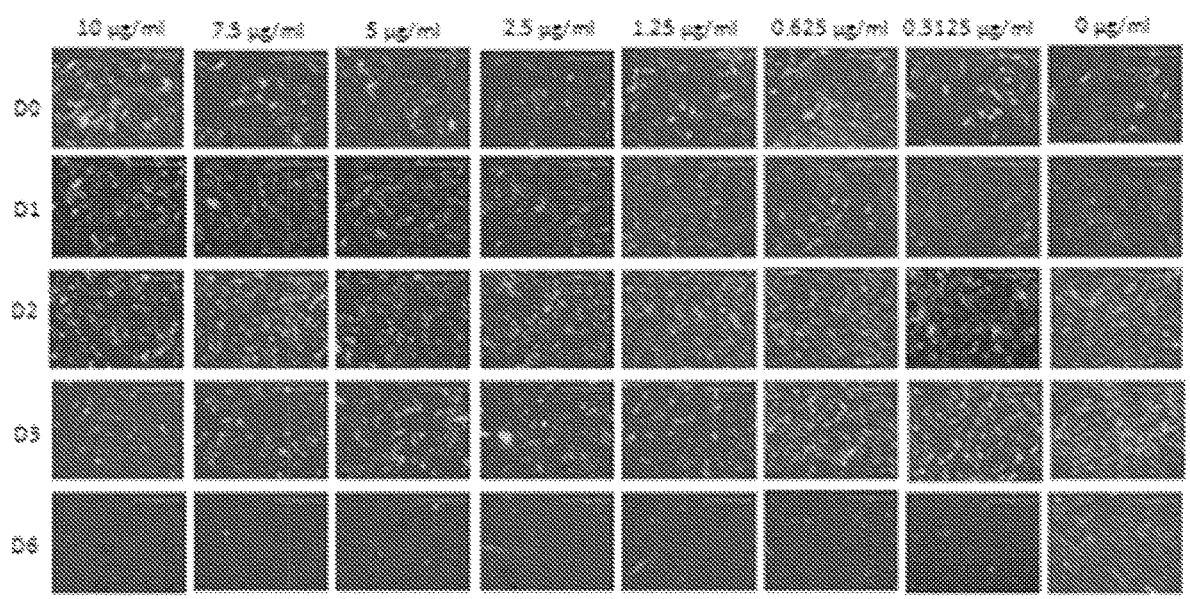

The disclosure will be further understood by those of skill in the art by reference to the below exemplary, non-limiting embodiments:

In some circumstance, tracking AVLP systems is desirable. To achieve this, Hyg-TK was fused with nano-luciferase (L) to generate AVLP-HTL (Hyg-TK-luciferase) (FIG. 20). All three proteins are functional, allowing positive selection of AVLP-HTL with hygromycin, negative selection with the TK gene, and tracking of the AVLP system with luciferase by standard methods (FIG. 23). Other luciferase genes, and other reporter genes may also be used.

Example 6

The disclosure will be further understood by those of skill in the art by reference to the below exemplary, non-limiting embodiments:

AVLP-CFTR variants were developed as therapeutic agents to express functional CFTR in primary human epithelial cells for CF (cystic fibrosis) patients (FIG. 22). To demonstrate functionality of the AVLP system in this target tissue, AVLP-EGFP systems were administered to primary human and pig epithelial cells and tracked. The cells were healthy after introduction of AVLP-EGFP and all continued to express EGFP at 42 days (FIG. 9).

Figure 9:
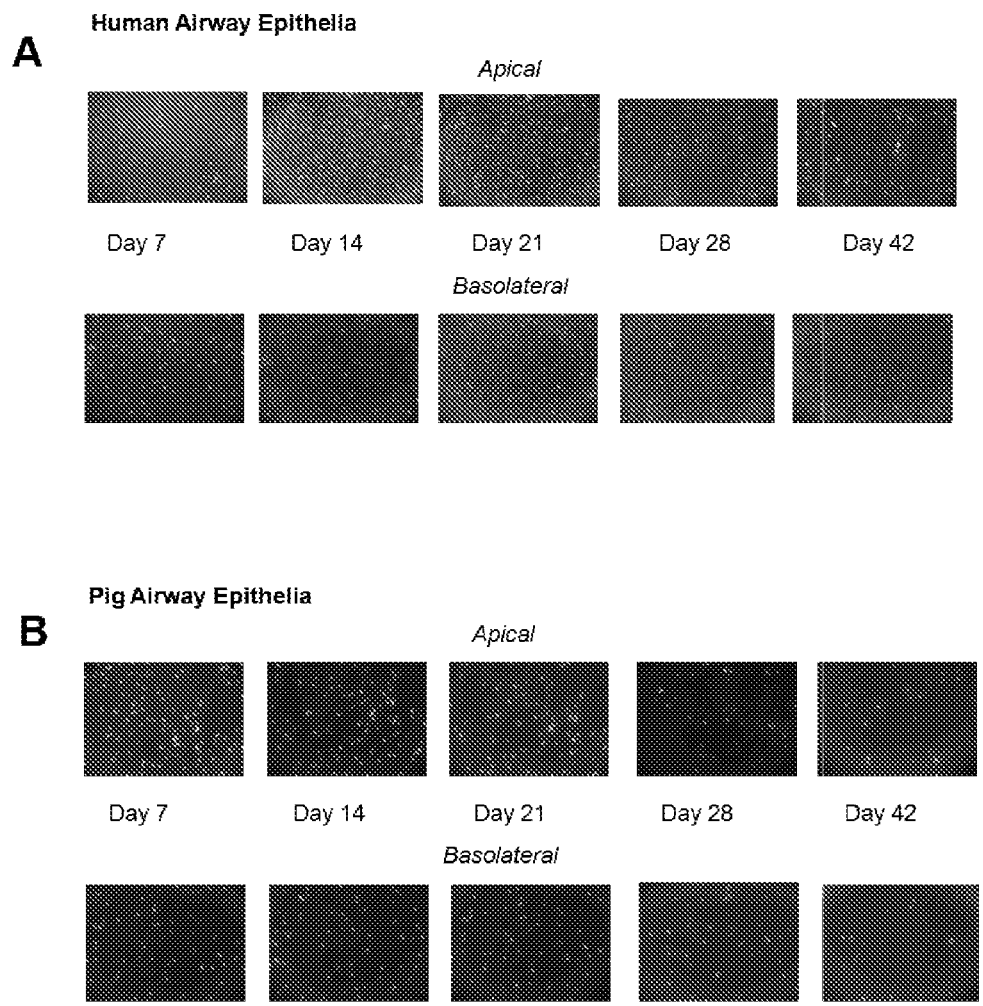

For reference, FIG. 9 shows AVLP-EGFP tested in primary human and pig airway epithelia cells. AVLP-EGFP caused minimal/non-detectable damage to the cells and expression of GFP was detected at 42 days after inoculation of the cells with AVLP-EGFP. Also, AVLP-EGFP could access the cells from both apical and basolateral surface of the cells. This demonstrates that AVLP system can be used to express genes in primary airway epithelial cells, which can be useful in for expression of heterologous nucleotide sequences of interest for use in the treatment certain diseases such, for example, cystic fibrosis therapy.

Example 7

Figure 11:
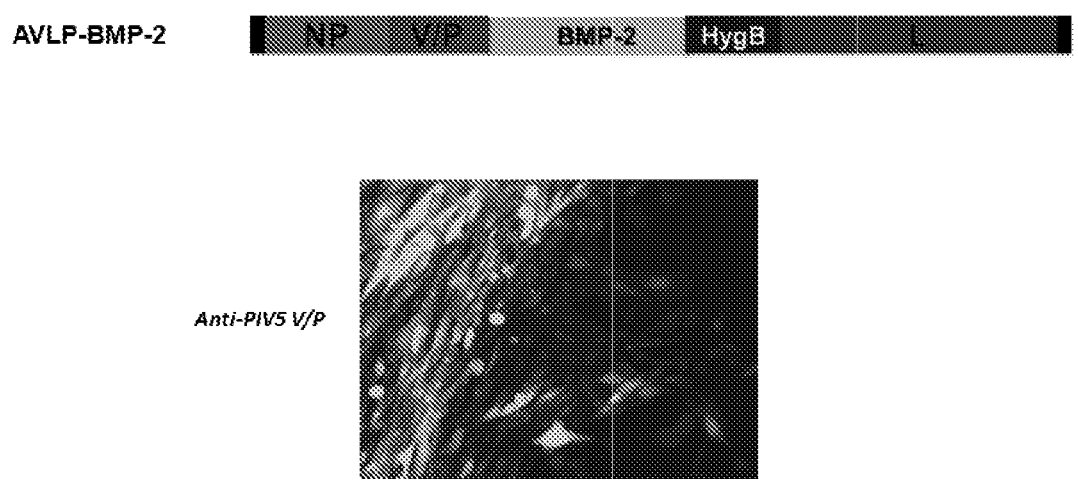
Figure 12:
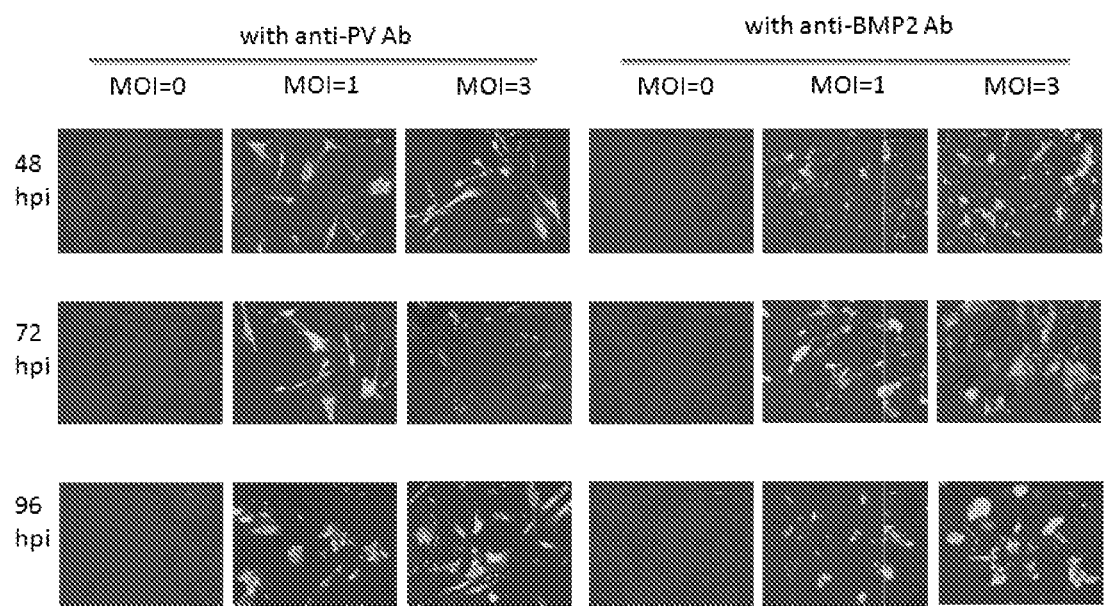
Figure 13:
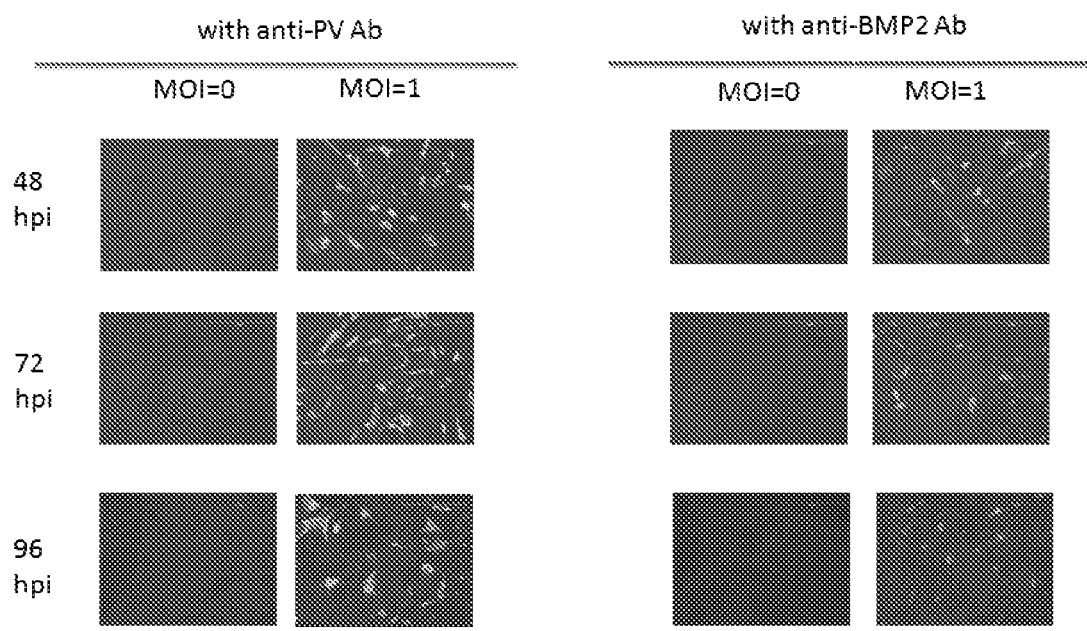
Figure 14:
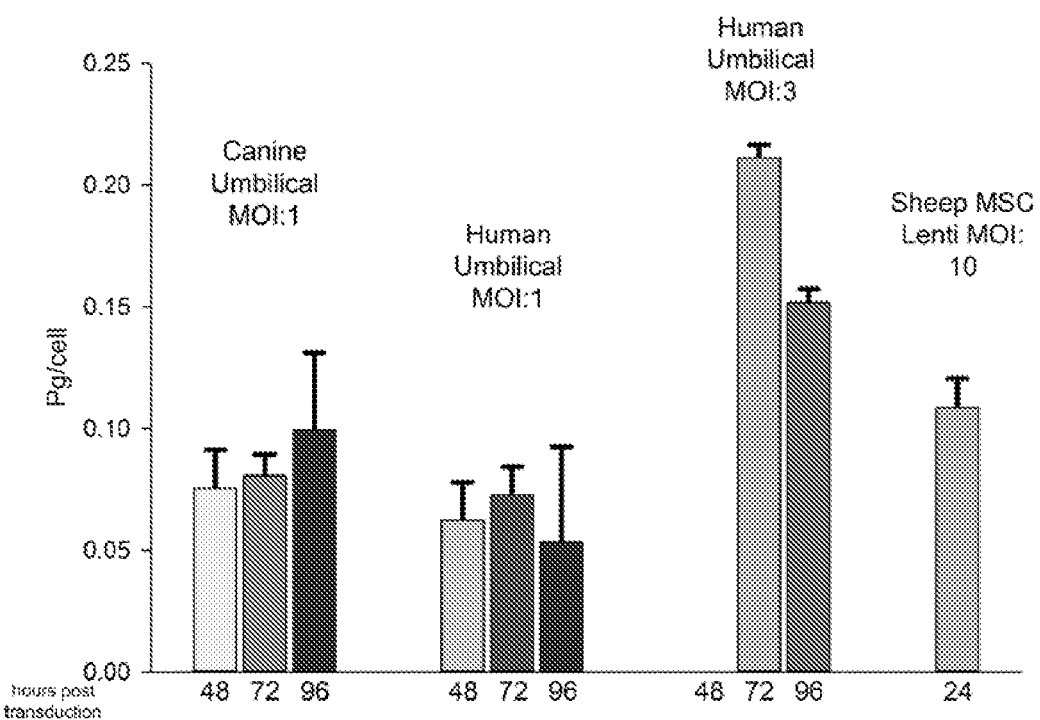
Figure 15:
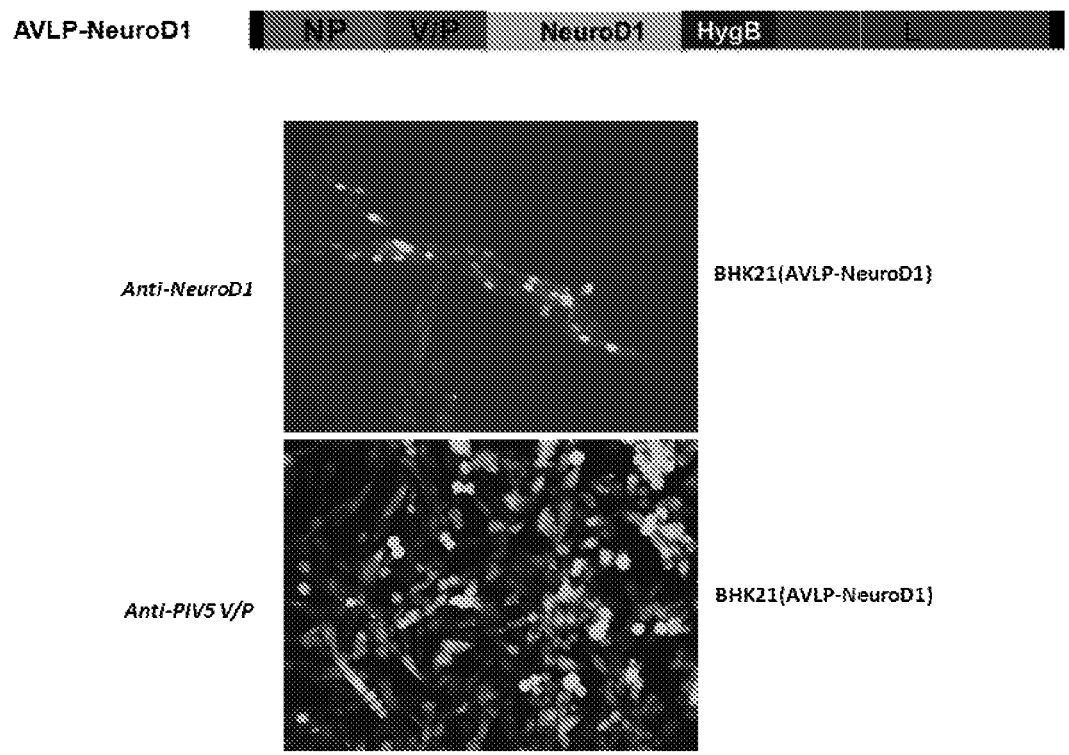

The disclosure will be further understood by those of skill in the art by reference to the below exemplary, non-limiting embodiments:

AVLP-BMP-2 systems were constructed (FIG. 11). The expression levels of AVLP-BMP-2 containing cells were higher than that of lentiviral vector-transduced cells. (FIG. 12, FIG. 13 and FIG. 14). Notably, AVLP-BMP-2 systems are less costly than lentiviral vector systems (more than 90% cheaper than lentiviral systems), and safer since they do not have a DNA-phase in their life cycle, and therefore do not integrate into host genome.

Example 8

Figure 10:
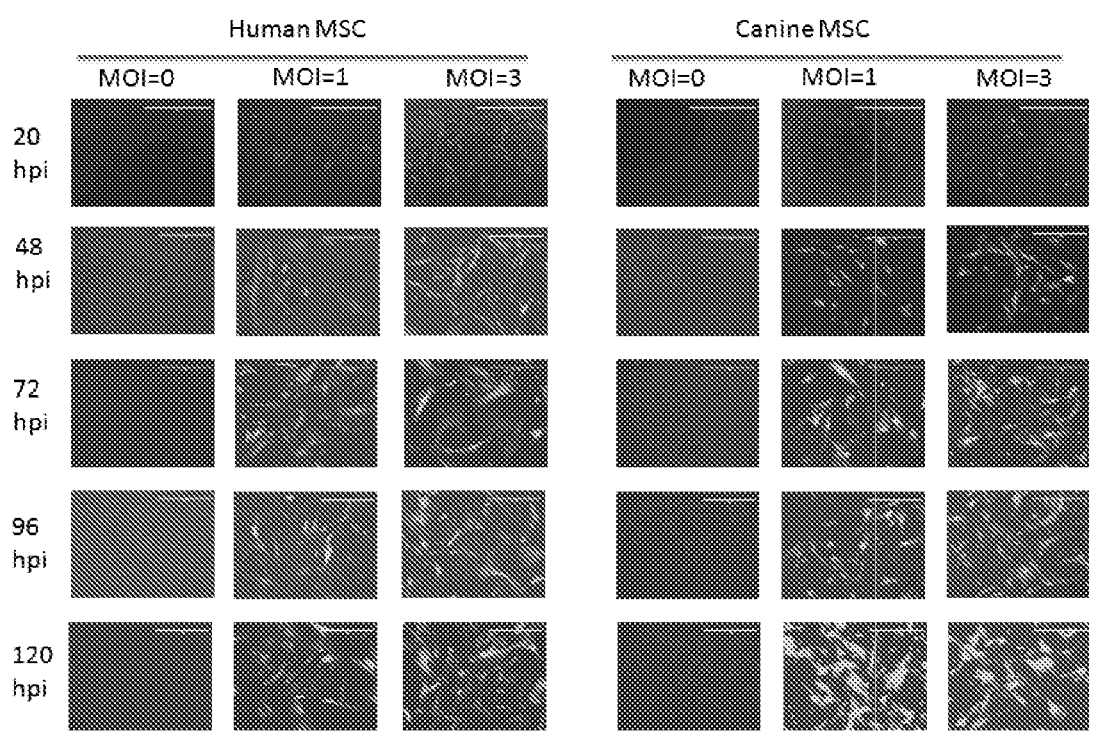

The disclosure will be further understood by those of skill in the art by reference to the below exemplary, non-limiting embodiments:

AVLP-EGFP were tested in human and canine mesenchymal stem cells (MSC). For reference, FIG. 10 shows AVLP-EGFP caused minimal/non-detectable damage to the cells and expression of GFP was detected at 5 days after inoculation of the cells with AVLP-EGFP. This further demonstrates that AVLPs can be used for MSC-based therapies.

Example 9

Figure 16:
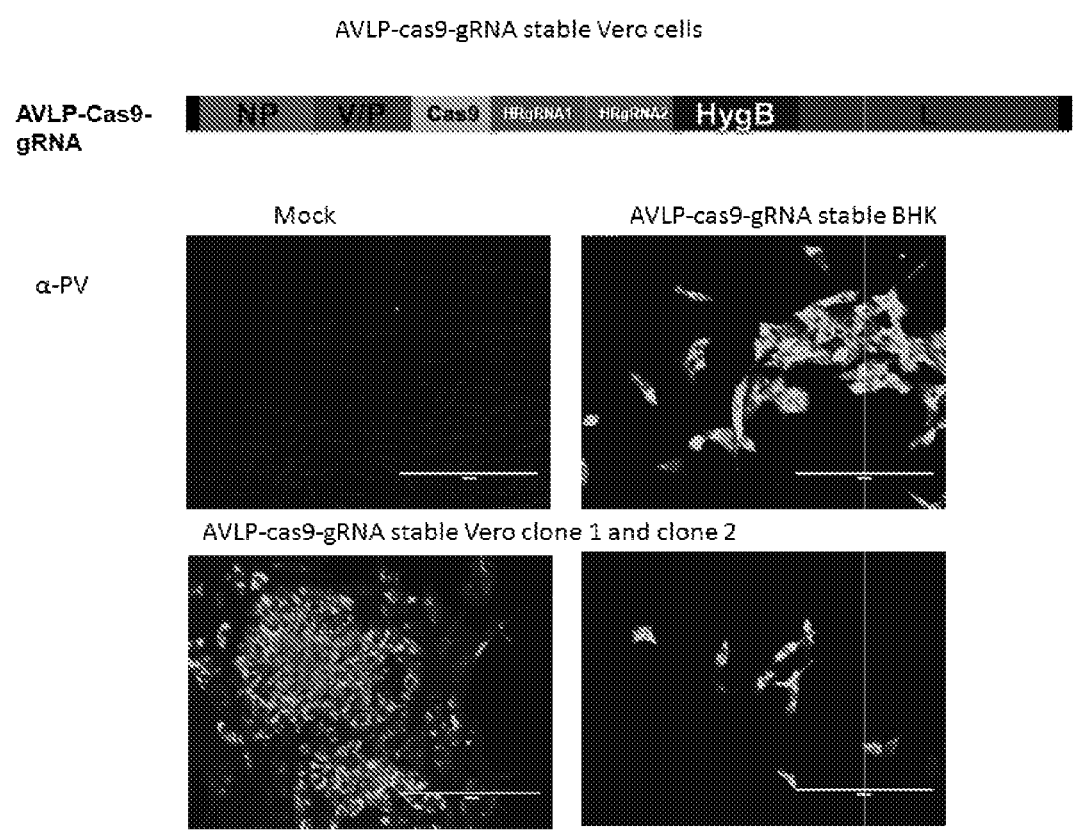
Figure 17:
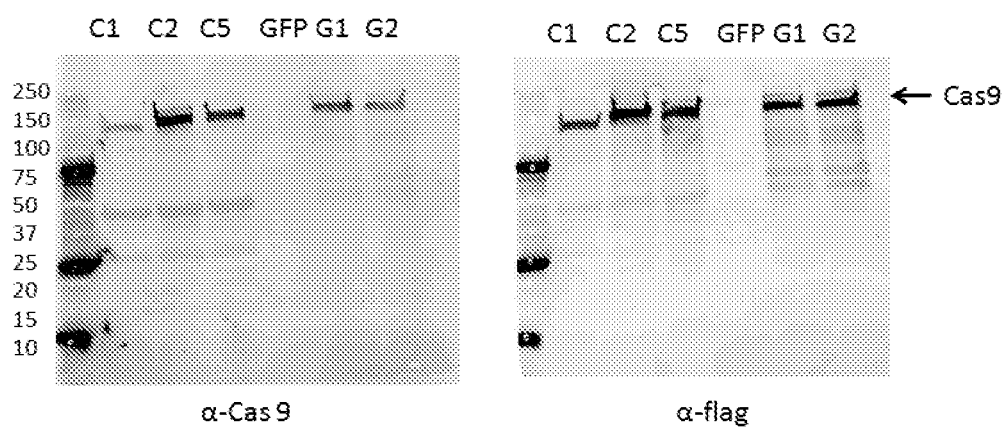

The disclosure will be further understood by those of skill in the art by reference to the below exemplary, non-limiting embodiments:

AVLP-Cas9 and guide RNA systems were demonstrated to express Cas9 and guide RNAs (FIG. 16 and FIG. 17).

Example 10

Figure 21:
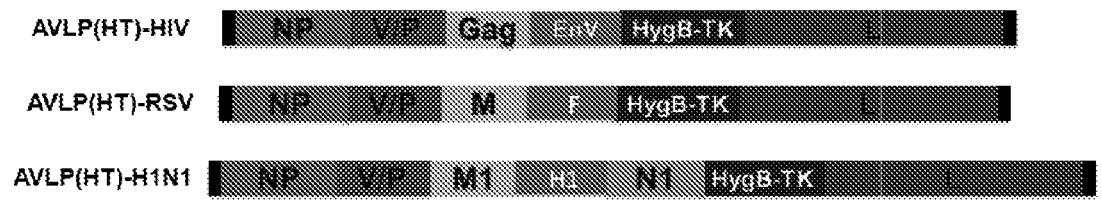
Figure 26:
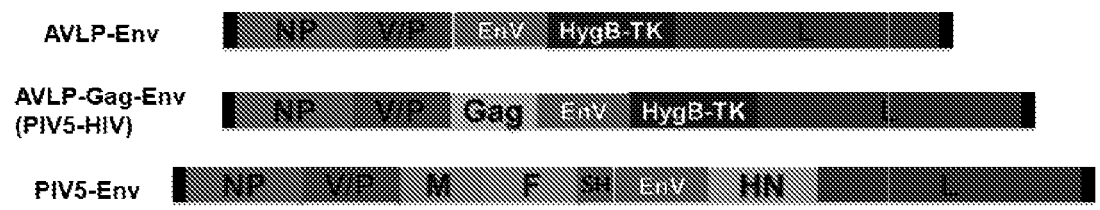
Figure 27:
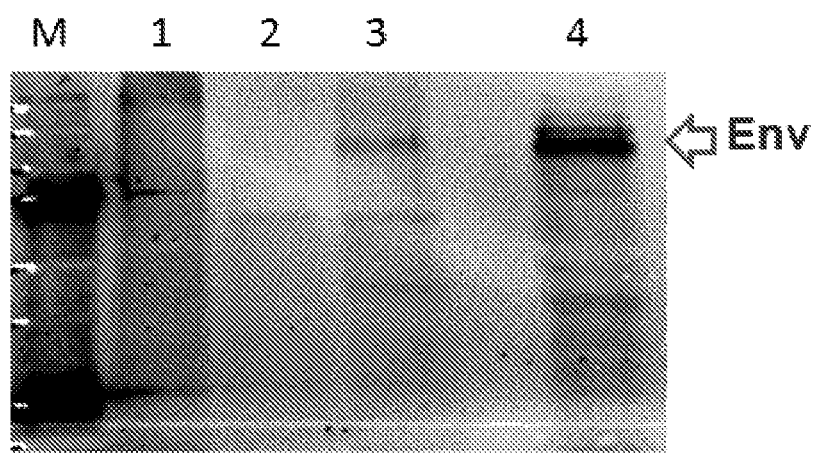

The disclosure will be further understood by those of skill in the art by reference to the below exemplary, non-limiting embodiments:

Taking advantage of the PIV5-AVLP system (which does not integrate into host cell genome like live HIV) a chimera PIV5-HIV was constructed containing Env and Gag of HIV, but internal proteins from PIV5 (FIG. 21, FIG. 26 and FIG. 27).

The expressible heterologous nucleotide sequence of interest may be incorporated into the AVLP-chimeric virus system to allow selection of PIV5-HIV growth with positive selection stimuli (e.g., hygromycin) and destruction of cells with PIV5-HIV with negative selection stimuli (e.g., acyclovir or ganciclovir).

Figure 18:
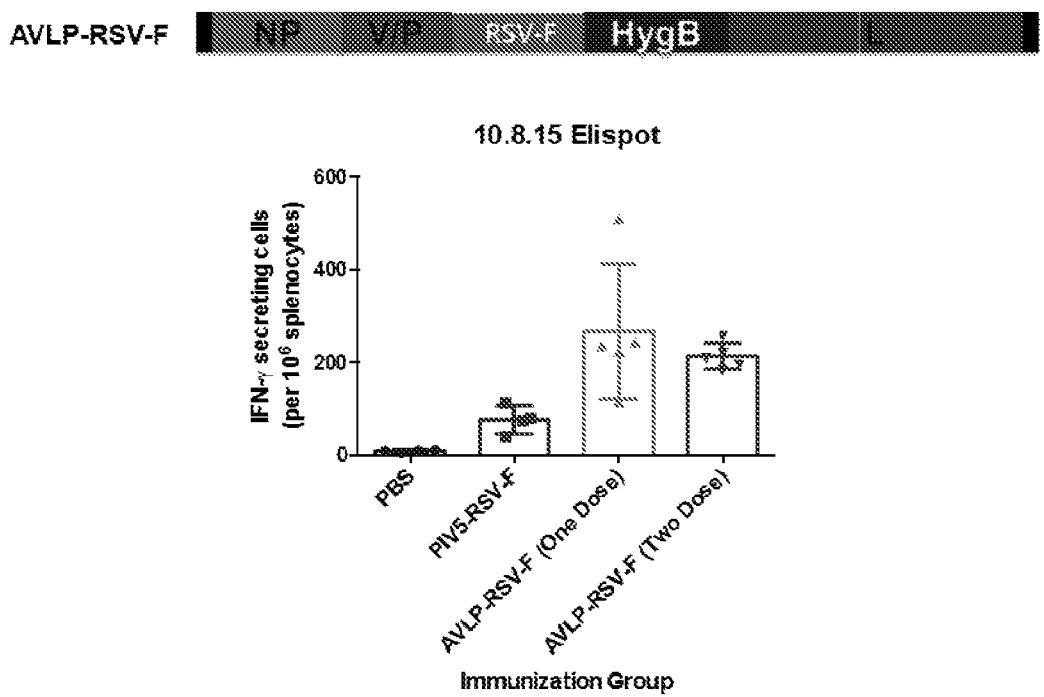

Besides PIV5-HIV, other chimera viruses may be generated. Non limiting examples include PIV5-RSV and PIV5-influenza H1N1 (FIG. 18, FIG. 20 and FIG. 21). To demonstrate the superior functionality of these AVLP systems, PIV5-RSV was shown to produce a far more robust immune response that non-amplifying virus particles having the same RSV F (FIG. 18).

For reference, splenocytes in FIG. 18 were mock-stimulated or stimulated with RSV-F peptide, GFP (irrelevant) peptide, or PMA/Ionomycin. AVLP immunization stimulated a better cell-mediated response than PIV5-RSV-F, indicating that AVLP-RSV-F generated robust cellular immune responses.

Example 11

The disclosure will be further understood by those of skill in the art by reference to the below exemplary, non-limiting embodiments:

AVLP-CART systems were constructed for potential use as a therapeutic agent in cancer therapy (FIG. 22). Other gene and/or sequence of interest for cancer gene therapy may also be used.

The present disclosure is not to be limited in scope by the specific embodiments described herein. Indeed, various modifications of the disclosure in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

We claim:

1. An amplifying virus-like particle consisting of:
   (i) an isolated polynucleotide sequence consisting of genes encoding a PIV5 nucleocapsid protein (NP), a PIV5 phosphoprotein (V/P) and a PIV5 large RNA polymerase (L), and
   (ii) an expressible heterologous non-PIV5 nucleotide sequence between the V/P and L genes.

2. The amplifying virus-like particle of claim 1, wherein the heterologous nucleotide sequence comprises a selection marker.

3. The amplifying virus-like particle of claim 2 wherein the selection marker is hygromycin (Hyg) or hygromycin and thymidine kinase fusion (Hyg-TK).

4. The amplifying virus-like particle of claim 1, wherein the heterologous nucleotide sequence encodes a molecule selected from the group consisting of miRNA, RNAi, shRNA, siRNA, antisense oligonucleotide, and ribozyme.

5. The amplifying virus-like particle of claim 1, wherein the heterologous nucleotide sequence is derived from a virus other than PIV5.

6. The amplifying virus-like particle of claim 5, wherein the heterologous nucleotide sequence is derived from a virus selected from the group consisting of influenza virus, RSV, and HIV.

7. The amplifying virus-like particle of claim 6, wherein the heterologous nucleotide sequence encodes influenza HA, RSV F, HIV Gag, or HIV Env.

8. The amplifying virus-like particle of claim 1, wherein the heterologous nucleotide sequence is a mammalian or bacterial sequence.

9. The amplifying virus-like particle of claim 1, wherein the heterologous nucleotide sequence encodes CFTR or NeuroD1 or BMP-2 protein.

10. The amplifying virus-like particle of claim 1, wherein the heterologous nucleotide sequence encodes Cas9 and guide RNAs.

11. The amplifying virus-like particle of claim 1, wherein the polynucleotide further comprises a reporter gene.

12. A vector comprising the amplifying virus-like particle polynucleotide of claim 1.

13. A host cell comprising the amplifying virus-like particle of claim 1.

14. A method of producing a plurality of amplifying virus-like particles, comprising:
   a) transfecting cells with the amplifying virus-like particle of claim 1 in combination with plasmids expressing PIV5 fusion protein (F), PIV5 hemagglutinin neuraminidase (1HN), and PIV5 matrix protein (M),
   b) collecting the amplifying virus-like particles from the supernatant; and
   c) infecting cells with virus containing F, HN and M.

15. A method of treating a disease in a subject in need thereof comprising administering to said subject the AVLP of claim 1.

* * * * *